(12) United States Patent
Rourke et al.

(10) Patent No.: US 12,340,329 B2
(45) Date of Patent: *Jun. 24, 2025

(54) MULTI-PLATFORM PRESCRIPTION ROUTING SYSTEM

(71) Applicant: Medimpact Healthcare Systems, Inc., San Diego, CA (US)

(72) Inventors: Timothy Rourke, San Diego, CA (US); William J. Barre, San Diego, CA (US)

(73) Assignee: MEDIMPACT HEALTHCARE SYSTEMS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/992,652

(22) Filed: Nov. 22, 2022

(65) Prior Publication Data

US 2024/0170119 A1    May 23, 2024

Related U.S. Application Data

(63) Continuation of application No. 16/159,471, filed on Oct. 12, 2018, which is a continuation of application
(Continued)

(51) Int. Cl.
*G06Q 10/0631* (2023.01)
*G06Q 10/10* (2023.01)
(Continued)

(52) U.S. Cl.
CPC ....... *G06Q 10/06315* (2013.01); *G06Q 10/10* (2013.01); *G06Q 30/0206* (2013.01);
(Continued)

(58) Field of Classification Search
CPC ... G16H 20/10; G06Q 10/06315; G06Q 40/08
See application file for complete search history.

(56) References Cited

U.S. PATENT DOCUMENTS

| 5,301,105 A | 4/1994 | Cummings, Jr. |
| 5,704,044 A | 12/1997 | Tarter et al. |

(Continued)

FOREIGN PATENT DOCUMENTS

| JP | 2003263499 A | 9/2003 |
| KR | 20010075839 A | 8/2001 |

(Continued)

OTHER PUBLICATIONS

AMCP Guide to Pharmaceutical Payment Methods, Comperhensive Edition, AMCP Task Force on Drug Payment Methodologies, Oct. 2007, 65 pages.

(Continued)

*Primary Examiner* — Sheetal R Paulson
(74) *Attorney, Agent, or Firm* — Mintz Levin Cohn Ferris Glovsky and Popeo, P.C.

(57) ABSTRACT

Systems and methods for a multi-platform prescription routing system in a network are provided. The system includes a network interface communicatively coupled to a computer network, the network interface including a receiver and a transmitter. The system includes at least one processor communicatively coupled to the network interface. The processor is configured to transmit the first prescription to the first supplier, and the second prescription to the second supplier for fulfillment. The processor is further configured to receive, via the network interface, status updates from the one or more suppliers. The processor is further configured to transmit, via the network interface, the status updates to the at least one user device in a format through which the status updates from the first supplier and the second supplier are together viewable by the patient within a single user interface at the user device.

20 Claims, 11 Drawing Sheets

Related U.S. Application Data

No. 14/776,614, filed as application No. PCT/US2014/026660 on Mar. 13, 2014, now abandoned.

(60) Provisional application No. 61/786,076, filed on Mar. 14, 2013.

(51) Int. Cl.
  G06Q 30/0201 (2023.01)
  G06Q 40/08 (2012.01)
  G16H 10/60 (2018.01)
  G16H 20/10 (2018.01)

(52) U.S. Cl.
  CPC ............ G06Q 40/08 (2013.01); G16H 10/60 (2018.01); G16H 20/10 (2018.01)

(56) References Cited

U.S. PATENT DOCUMENTS

| | | |
|---|---|---|
| 5,737,539 A | 4/1998 | Edelson et al. |
| 5,845,255 A | 12/1998 | Mayaud |
| 6,108,635 A | 8/2000 | Herren et al. |
| 6,195,612 B1 | 2/2001 | Pack-Harris |
| 6,283,761 B1 | 9/2001 | Joao |
| 6,341,265 B1 | 1/2002 | Provost et al. |
| 7,165,077 B2 | 1/2007 | Kalies, Jr. |
| 7,412,396 B1 | 8/2008 | Haq |
| 7,490,047 B2 | 2/2009 | Brown et al. |
| 7,505,917 B2 | 3/2009 | Howe et al. |
| 7,685,026 B1 | 3/2010 | McGrady et al. |
| 7,769,601 B1 | 8/2010 | Bleser et al. |
| 7,840,424 B2 | 11/2010 | Wiley et al. |
| 7,949,580 B1 | 5/2011 | Boyer et al. |
| 8,060,379 B1 | 11/2011 | Pinsonneault et al. |
| 8,069,059 B2 | 11/2011 | Howe et al. |
| 8,099,295 B2 | 1/2012 | Virdee et al. |
| 8,265,950 B2 | 9/2012 | Howe et al. |
| 8,346,571 B2 | 1/2013 | Kalies, Jr. |
| 8,433,587 B1 | 4/2013 | Cullen |
| 8,447,628 B2 | 5/2013 | Kalies, Jr. |
| 8,788,282 B2 | 7/2014 | Watanabe |
| 8,844,803 B2 * | 9/2014 | Utech ............... G16H 40/40 700/226 |
| 2001/0037216 A1 | 11/2001 | Oscar et al. |
| 2002/0002495 A1 | 1/2002 | Ullman |
| 2002/0049617 A1 | 4/2002 | Lencki et al. |
| 2002/0082863 A1 | 6/2002 | Kleinke |
| 2002/0095316 A1 | 7/2002 | Toan et al. |
| 2002/0111832 A1 | 8/2002 | Judge |
| 2002/0120473 A1 | 8/2002 | Wiggins |
| 2002/0147617 A1 | 10/2002 | Schoenbaum et al. |
| 2002/0169727 A1 | 11/2002 | Melnick et al. |
| 2002/0183965 A1 | 12/2002 | Gogolak |
| 2003/0154106 A1 | 8/2003 | Marks |
| 2003/0195771 A1 | 10/2003 | Fitzgerald et al. |
| 2004/0039604 A1 | 2/2004 | Tallal, Jr. |
| 2004/0054685 A1 | 3/2004 | Rahn et al. |
| 2004/0073457 A1 | 4/2004 | Kalies, Jr. |
| 2004/0122713 A1 | 6/2004 | Hill et al. |
| 2004/0133452 A1 | 7/2004 | Denny et al. |
| 2004/0143171 A1 | 7/2004 | Kalies, Jr. |
| 2004/0143594 A1 | 7/2004 | Kalies, Jr. |
| 2004/0148194 A1 | 7/2004 | Wellons et al. |
| 2004/0148195 A1 | 7/2004 | Kalies, Jr. |
| 2004/0148196 A1 | 7/2004 | Kalies, Jr. |
| 2004/0148198 A1 | 7/2004 | Kalies, Jr. |
| 2004/0148498 A1 | 7/2004 | Circenis et al. |
| 2004/0230502 A1 | 11/2004 | Fiacco et al. |
| 2005/0060188 A1 | 3/2005 | Valley |
| 2005/0065821 A1 | 3/2005 | Kalies, Jr. |
| 2005/0071193 A1 | 3/2005 | Kalies, Jr. |
| 2005/0071200 A1 | 3/2005 | Franklin et al. |
| 2005/0240442 A1 | 10/2005 | Lapsker |
| 2005/0251429 A1 | 11/2005 | Ammer et al. |
| 2005/0261939 A1 | 11/2005 | Augspurger et al. |
| 2005/0283259 A1 | 12/2005 | Wolpow |
| 2006/0020514 A1 | 1/2006 | Yered |
| 2006/0116905 A1 | 6/2006 | Yered |
| 2006/0129357 A1 | 6/2006 | Francis et al. |
| 2006/0178915 A1 | 8/2006 | Chao |
| 2006/0182705 A1 | 8/2006 | Cruse |
| 2006/0184391 A1 | 8/2006 | Barre et al. |
| 2006/0271402 A1 | 11/2006 | Rowe et al. |
| 2007/0011025 A1 | 1/2007 | Cracchiolo et al. |
| 2007/0025031 A1 | 2/2007 | Kwon |
| 2007/0050210 A1 | 3/2007 | Wiley, II |
| 2007/0106623 A1 | 5/2007 | Melnick et al. |
| 2007/0233516 A1 | 10/2007 | Howe et al. |
| 2007/0233526 A1 | 10/2007 | Hoffman et al. |
| 2007/0250341 A1 | 10/2007 | Howe et al. |
| 2008/0183492 A1 | 7/2008 | Warren et al. |
| 2008/0228519 A1 | 9/2008 | Leon |
| 2008/0312956 A1 | 12/2008 | Momita et al. |
| 2009/0076868 A1 | 3/2009 | Malone et al. |
| 2009/0083064 A1 * | 3/2009 | Mahinda ............... G06Q 30/00 705/2 |
| 2009/0144082 A1 | 6/2009 | Selbst et al. |
| 2009/0177488 A1 | 7/2009 | Unland et al. |
| 2009/0177490 A1 | 7/2009 | Howe et al. |
| 2009/0281823 A1 | 11/2009 | Hardaway |
| 2009/0281824 A1 | 11/2009 | Hardaway |
| 2009/0319311 A1 | 12/2009 | Mi et al. |
| 2009/0326975 A1 | 12/2009 | Hardaway et al. |
| 2010/0057489 A1 * | 3/2010 | Howe .................. G06Q 20/102 705/40 |
| 2010/0161351 A1 | 6/2010 | Howe et al. |
| 2010/0217622 A1 | 8/2010 | Brown et al. |
| 2010/0287002 A1 | 11/2010 | Barre et al. |
| 2010/0312578 A1 | 12/2010 | Hardaway |
| 2011/0029321 A1 | 2/2011 | Rourke et al. |
| 2011/0054935 A1 | 3/2011 | Hardaway |
| 2011/0246232 A1 * | 10/2011 | Starko .................... G06Q 20/14 705/2 |
| 2012/0253829 A1 | 10/2012 | John et al. |
| 2013/0144649 A1 * | 6/2013 | Kalies, Jr. ............. G06Q 30/02 705/2 |
| 2014/0278495 A1 | 9/2014 | Rourke et al. |
| 2016/0034668 A1 | 2/2016 | Rourke et al. |
| 2017/0161458 A1 | 6/2017 | Rourke et al. |
| 2019/0279753 A1 | 9/2019 | Rourke et al. |

FOREIGN PATENT DOCUMENTS

| | | |
|---|---|---|
| WO | 9524010 A1 | 9/1995 |
| WO | 9744752 A1 | 11/1997 |
| WO | 2014151911 A1 | 9/2014 |

OTHER PUBLICATIONS

Bank of America and Caremark Introduce Pharma Rewards Credit Card, http://www.banking-business-review.com/news/bank_of_america_and_caremark_introduce_pharma_r, Oct. 27, 2006, 1 page.

Centers for Medicare & Medicaid Services (CMS), 2006 Prescription Drug Event Data Training Participant Guide, Jul. 2006, pp. 1-222.

CitiBusiness Credit Cards Free Prescription Discount Program, Payment News, May 11, 2006, 3 pages.

CitiBusiness(R) Credit Cards Announces New Card member Benefit Free Prescription Discount Program, http:/Mw-N.prnewswire.com/cgi-bin/stories.pl?ACCT=104&STORY=/ww, Jun. 10, 2009, 2 pages.

Comments of Generic Pharmaceutical Association for the Public Meeting on Proposed Changes to the National Drug Code System, Nov. 24, 2006, 7 pages.

Cost Sharing Strategies for OHP Medical Services, revised Jul. 5, 2001, pp. 1-5.

Credit Cards Offer Discounts on Prescription Drugs, http://wbztv.com/consumer/credit.Card.Discounts.2.682345.html, Mar. 26, 2008, 2 pages.

CVS to Buy MinuteClinic Walk-In Medical Service, Los Angeles Times, Jul. 14, 2006, 1 page.

(56) References Cited

OTHER PUBLICATIONS

Florida House of Representatives, Enrolled CS/HB 535, Legislature, 2008, 5 pages.
International Search Report received for PCT Application No. PCT/US2014/026660, mailed on Aug. 4, 2014, 8 pages.
MedImpact Medicare Part D 2008 Pre-Processing Drug List (PPDL) White Paper, Mar. 25, 2008, pp. 1-5.
MedImpact Medicare Part D 2009 Pre-Processing Drug List (PPDL) White Paper, MedImpact, Mar. 25, 2008, pp. 1-5.
MedImpact Medicare Part D Drug List White Paper, Oct. 13, 2005, pp. 1-4.
MedImpact Medicare Part D Pre-Processing Drug List (PPDL) White Paper, MedImpact, Updated Jul. 20, 2006, pp. 1-5.
PCT International Preliminary Report on Patentability received for Application No. PCT/US2014/026660, mailed on Sep. 15, 2015, 7 pages.
International Search Report and Written Opinion for International PCT Application No. PCT/US06/042976, mailed Sep. 11, 2007.
Prescription Card, Union Plus Health Savings Presicription Card, Jun. 6, 2009, 2 pages.
EPN—Electronic Prescribing News, Systems Xcellence Announces Three-Year $4.0 Million Software License, Support and Operations Contract, Nov. 9, 2005, 2 pages.
Walgreens Store Green Dot Prepaid MasterCard and Visa cards, Available on: http://www.walgreens.com/store/promotion/greendot/default.jsp, Jun. 10, 2009, 2 pages.
"Requirements for Submitting Prescription Drug Event (PDE) Data", Department of Health and Human Services, Centers for Medicare and Medicaid Services, Apr. 27, 2006, pp. 1-92.
Federal Register (May 16, 2008) "Medicare Program; Revisions to the Medicare Advantage and Prescription Drug Benefit Programs", Department of Health and Human Services (HHS), 66 pages.
Huskamp et al. (Mar.-Apr. 2000) "The Medicare Prescription Drug Benefit: How Will the Game be Played?", Health Affairs, 19(2):8-23.
Laing et al. (Feb. 2007) "Tuberculosis Drug Issues: Prices, Fixed Dose Combination Products and Second Line Drugs", Journal Tuberculosis Disease, 4(12):S194-S207.
Lipton et al. (Mar.-Apr. 2000) "Managing the Pharmacy Benefit in Medicare HMOs: What Do We Really Know?", Health Affairs, 19(2):42-58.
"Prescription Drug Event (PDE) Submission Process Summary", Infocrossing Healthcare Services, Infocrossing, 2007, pp. 1-2.
"American Inventor Develops Method for Competitive Prescription Drug and/or Bidding Service Provider Selection", ProQuest, May 11, 2010, 2 pages.

* cited by examiner

MULTI-PLATFORM PRESCRIPTION ROUTING SYSTEM

CROSS REFERENCE TO RELATED APPLICATION

This application claims the benefit of and priority to and is a continuation of U.S. patent application Ser. No. 16/159,471, filed on Oct. 12, 2018, which is a continuation of U.S. patent application Ser. No. 14/776,614, filed on Sep. 14, 2015, which is a national phase application that claims priority to international application PCT/US2014/026660, filed on Mar. 13, 2014, which claims priority to and benefit of U.S. Provisional Application 61/786,076, filed on Mar. 14, 2013, the entirety of each of which is incorporated by reference herein.

BACKGROUND

Technical Field

The present technology relates to systems and methods for routing pharmaceutical claims over a network. More particularly, the present technology relates to computer architecture and operating methods for multi-platform prescription routing.

Description of Related Art

Computing systems can include a processor, a memory, a storage device, and input/output devices. The processor, the memory, the storage device, and the input/output devices can be interconnected via a system bus. The processor is capable of processing instructions for execution within the computing system. Such executed instructions can implement one or more components of, for example, a cloud platform. The computing system may include input/output devices that can provide input/output operations for a network device. For example, the input/output device can include Ethernet ports or other networking ports to communicate with one or more wired and/or wireless networks (e.g., a local area network (LAN), a wide area network (WAN), the Internet) or hardware or software implemented communications switches placed within the networked environment. Additionally, some computing devices may present difficulties related to navigating interfaces quickly and efficiently to access data and activate a desired function. In particular, user interfaces that present significant amounts of data tend to need functionality divided into layers or views. With conventional user interfaces, a user may need to scroll around and switch views many times to find the right data/functionality. An effective user interface would ideally enable the user to readily and rapidly access the right data/functionality.

In conventional network systems, computing systems select one repository for storing data in one logical database across a network. Conventional computing systems typically retrieve data from and store data on their own systems. A computing system may remotely access one of a plurality of server systems across a network that might in turn access the database system. Data retrieval from the system might include the issuance of a request from the user system to the database system. The database system may process the request for information and send to the user system information relevant to the request. The rapid and efficient retrieval of accurate information is critical to routing claims over a computer network environment in which a plurality of computing systems access and retrieve data from a plurality of databases coupled to a communications network.

Many computing systems coordinate and/or generate claims over a network to have patient pharmaceutical costs covered through prescription benefit plans ("plans"). These plans are generally offered to patients through health maintenance organizations, employer groups, and government entities ("payers"). Under such plans, a patient receives an electronic prescription for a medication from his or her physician and submits it to a pharmacy computing system to be filled. The pharmacy computing system checks to see that the patient is a member of a plan with which the pharmacy has an agreement and that the medication and dosage prescribed are within the approved scope of the plan agreement. Upon verification of these requirements, the pharmacy computing system instructs the dispensing of the medication to the patient. The patient pays the pharmacy computing system a copayment amount ("copay"), which is less than the normal cost of the medication. The pharmacy computing system must request, and wait to receive, the balance of the payment for the medication and its dispensing services from a prescription benefit manager ("PBM") with whom the payer has agreed to manage the plan. The PBM invoices the payer (i.e., the PBM's customer) for the patient's transaction, along with a charge for the agreed fee. From the funds paid by the payer, the PBM pays the pharmacy's balance due. In such a computing system, payers typically turn to PBMs to manage costs. Because the cost of medications is so high and is such a large component of medical care costs generally, there is an on-going effort on the part of PBMs and payers to seek ways to control medication costs. As all healthcare costs continue to rise, there is also an ongoing need for more controlled cost management of patients' other healthcare needs.

SUMMARY

The systems and methods described herein each have several aspects, no single one of which is solely responsible for its desirable attributes. Without limiting the scope of this disclosure as expressed by the claims that follow, the more prominent features will now be discussed briefly. After considering this discussion, and particularly after reading the section entitled "Detailed Description," one will understand how the sample features described herein provide for a more comprehensive system having several advantages over current prescription drug fulfillment systems.

The systems and methods described herein relate to a total healthcare needs fulfillment system. The healthcare needs fulfillment system of various embodiments is a computer-based central computing system which facilitates coordination between multiple parties, such as physicians, suppliers such as pharmacies and specialty providers, and patients, in order to provide some of or all the medical goods and services needed by a patient. In various embodiments, the computer-based healthcare needs fulfillment system is owned, managed, and/or operated by a prescription benefits manager (PBM) and a patient's prescription-related interactions center around the PBM and the PBM's system. In certain embodiments, the system largely eliminates the need for a patient to communicate with a fulfilling supplier such as a pharmacy. Such a system creates new opportunities for distributing prescriptions to suppliers for fulfillment and new opportunities for delivering prescriptions and health-related content to patients.

In some embodiments, the healthcare needs fulfillment system includes a web-based or mobile interface through which patients can monitor and manage their healthcare needs. The interface of some embodiments displays all of a patient's prescribed medical goods and services across suppliers—even if several suppliers are providing the various goods and services. In some such embodiments, a patient can, within the user interface, track the status of each prescribed good and service, monitor adherence to treatment plans across suppliers, and provide financial information to facilitate automatic payment to various suppliers.

In certain embodiments, the healthcare needs fulfillment system also provides content, downloadable applications, and/or web-based interfaces designed to push healthcare management downstream to patients and empower patients. For example, the healthcare needs fulfillment system of some embodiments generates and provides alerts to a patient if potential drug interactions are identified or if relevant health and wellness tips, reminders, and/or tools become available. The system of some embodiments provides a patient with personalized, curated content related to health topics determined to be of relevance to the patient based on the patient's prescribed goods and services, documented health conditions, historical usage of the system, self-identified preferences, etc.

One aspect of the disclosure is directed to a method for fulfilling and managing prescriptions. In some embodiments, the method is implemented by a specialized PBM computer, such as a computer that is owned, managed, and/or controlled by a PBM (or other manager of health plans, programs, and/or prescriptions); such a computer is programmed to concurrently manage prescriptions for a multitude of patients. In certain embodiments, the method includes: electronically receiving a plurality of prescriptions for a patient from one or more users' computers, wherein each of the plurality of prescriptions identifies the patient and a prescribed treatment; selecting supplier selection criteria to apply to the plurality of prescriptions; applying the supplier selection criteria to automatically select one or more fulfilling suppliers from a set of certified suppliers, wherein each of the fulfilling suppliers is selected to fill one or more of the plurality of prescriptions; transmitting the plurality of prescriptions to the respective fulfilling suppliers for fulfillment; receiving status updates from each of the fulfilling suppliers, wherein the status updates comprise prescription receipt confirmation, fulfillment confirmation, and shipment confirmation; and transmitting the status updates to a patient's computer in a format through which the status updates from all the fulfilling suppliers are together viewable by the patient within a single user interface.

In some embodiments, the method also includes adjudicating and authorizing fulfillment of each of the plurality of prescriptions. In certain embodiments, adjudicating and authorizing fulfillment occurs prior to transmitting the plurality of prescriptions to the respective fulfilling suppliers for fulfillment. Additionally or alternatively, in some embodiments, the method includes: calculating a copayment price owed by the patient for each of the plurality of prescriptions; accessing account information for a financial account of the patient from a database; deducting the copayment price from the financial account; and transmitting a payment to each of the fulfilling suppliers. In some embodiments, one payment is transmitted to each fulfilling supplier, the payment including the copayment price owed by the patient and the price owed by the plan payer.

In some embodiments, the method additionally or alternatively includes: identifying the patient from each of the plurality of prescriptions; searching a database to identify a plan to which the patient belongs; and searching a database to identify the supplier selection criteria associated with the plan. In some such embodiments, selecting supplier selection criteria to apply to the plurality of prescriptions involves selecting the identified supplier selection criteria associated with the plan to which the patient belongs.

In certain embodiments, the supplier selection criteria includes a set of rules dictating how the set of certified suppliers are to be evaluated to select the plurality of suppliers. In some such embodiments, applying the supplier selection criteria includes evaluating the set of certified suppliers and selecting the fulfilling suppliers based on total price of adjudication. For example, in some embodiments, for each of the plurality of prescriptions, the certified supplier offering the lowest total price is selected. The lowest total price of adjudication may be determined, for example, from a list of prices submitted by the suppliers and/or through a competitive bidding process. In some embodiments, total price includes the price of the prescribed healthcare good or service and any associated fulfillment fees or other service fees charged by the supplier. In some embodiments, the fulfilling suppliers are selected based on a combination of total price of adjudication, performance rating, and/or ancillary service offerings. In other embodiments, the fulfilling suppliers may be selected based on supplier preferences specified by the payer for a particular plan.

In some embodiments of the method, the set of certified suppliers is formed of, and limited to, suppliers that have met a minimum level of service requirements and have integrated into a healthcare needs fulfillment system operated by the PBM or other prescription, program, or plan manager.

Another aspect of the disclosure is directed to a computing system for prescription fulfillment and management, the computing system formed of, at least, a processor, a receiver, and a transmitter configured to operate together to perform a method of fulfilling and managing prescriptions. In some embodiments, the processor is configured such that the processor, receiver, and transmitter perform any of the method embodiments described above.

In yet another aspect of the disclosure, the technology is directed to a non-transitory machine-readable storage medium embodying a set of instructions that, when executed by a processor, cause the processor to perform operations or methods, such as, for example, a method of fulfilling and managing prescriptions. In some embodiments, the instructions cause the processor to perform any of the method embodiments described above.

An additional aspect of the disclosure is directed to a method of selecting a supplier to fulfill future prescriptions via a bidding process. In some embodiments, the method includes transmitting an electronic link to a set of certified suppliers, wherein the link connects the set of certified suppliers to a bidding site. The method may further include setting minimum requirements that each bid needs to meet in order to be accepted. In some embodiments, the method also includes receiving one or more bids submitted by one or more of the certified suppliers, wherein each bid includes a price at which the submitting supplier would fill a prescription received for a healthcare good or service during a next time period. The method may further include automatically selecting a winning bid for each healthcare good or service, wherein: each new prescription for a healthcare good or service received during the next time period is sent to the supplier submitting the winning bid for the respective healthcare good or service, and the new prescription is filled by the respective supplier according to the terms set forth in the winning bid until the new prescription expires. In some embodiments, the winning bid is selected based at least in part on price. For example, in some embodiments, the lowest price bid is selected to be the winning bid. In some embodiments, the winning bid is additionally or alternatively selected based at least in part on the quantity or quality of ancillary services offered by submitting suppliers; for example, in some embodiments, the winning bid is the bid that includes the greatest quantity or quality of ancillary services as compared among various submitting suppliers that submitted a bid below a threshold price.

In some embodiments of the method, each bid submitted by a certified supplier is viewable by the set of certified suppliers, and each certified supplier is permitted to submit a plurality of bids during a duration of the bidding process. In other embodiments, only a current top bid is viewable by the set of certified suppliers at any particular time during the bidding process. In still other embodiments, a certified supplier's bid is submitted confidentially and is not viewable by other certified suppliers.

In some embodiments, a method for fulfilling and managing prescriptions is provided, which is implemented by a specialized PBM or other prescription management computer programmed to concurrently manage prescriptions for a multitude of patients. The method may include electronically receiving a prescription for a patient. In some embodiments, the method also includes conducting a bidding process, which is the same, substantially similar, or similar to the bidding process described above. The method may further include determining if, through the bidding process, a winning bid was received for a particular healthcare good or service. No winning bid was received if no certified supplier submitted an acceptable bid for the healthcare good or service. In some embodiments, when no winning bid has been received, the method for fulfilling the prescription further includes one of the following: transmitting the prescription to a selected certified supplier selected to fill one or more additional prescriptions for the patient, wherein the selected supplier submitted the winning bid or bids for the one or more additional prescriptions; transmitting the prescription to a certified supplier identified as having an expertise in a health condition associated with the healthcare good or service; or bundling a plurality of goods or services without winning bids together to form bundled packages and providing an electronic link to the set of certified suppliers to bid on the bundled packages. In some embodiments where the goods and services are bundled, the prescription is transmitted to the supplier that submits a winning bid on the bundled package that includes the prescribed healthcare good or service.

Another aspect of the disclosure is directed to a computing system for selecting a supplier to fulfill future prescriptions via a bidding process, the computing system formed of, at least, a processor, a receiver, and a transmitter configured to operate together to perform a method of selecting suppliers via a bidding process. In some embodiments, the processor is configured such that the processor, receiver, and transmitter perform an embodiment of the method described above.

In yet another aspect of the disclosure, the technology is directed to a non-transitory machine-readable storage medium embodying a set of instructions that, when executed by a processor, cause the processor to perform operations or methods, such as, for example, a method of selecting a supplier to fulfill future prescriptions via a bidding process. In some embodiments, the instructions cause the processor to perform an embodiment of the method described above.

A further aspect of the disclosure is directed to a method of curating electronic health content relevant to a health state of a patient. The method of various embodiments is implemented by a specialized computer programmed to concurrently curate electronic health content for a multitude of patients. In some embodiments, the method includes: electronically receiving a prescription, which identifies a prescribed treatment for a patient; identifying a health condition or a category of health conditions the patient is likely to have based on the prescribed treatment for the patient; identifying content recommended for patients having the health condition or the category of health conditions; and delivering the content to the patient.

In some embodiments, delivering the content to the patient involves transmitting an electronic link to the patient within a computer user interface to electronically connect the patient to the content. In some embodiments, the content is a web-based or mobile application. Additionally or alternatively, in some embodiments, identifying the health condition or the category of health conditions the patient is likely to have includes searching a database to identify a product classification or service classification to which the prescribed treatment belongs; in such embodiments, treatments are grouped into classifications based on the types of conditions they are tailored to treat.

Another aspect of the disclosure is directed to a computing system for curating electronic health content relevant to a health state of a patient. In various embodiments, the computing system is formed of, at least, a processor, a receiver, and a transmitter configured to operate together to perform a method of curating electronic health content relevant to a health state of a patient. In some embodiments, the processor is configured such that the processor, receiver, and transmitter perform an embodiment of the method described above.

In yet another aspect of the disclosure, the technology is directed to a non-transitory machine-readable storage medium embodying a set of instructions that, when executed by a processor, cause the processor to perform operations or methods, such as, for example, a method of curating electronic health content relevant to a health state of a patient. In some embodiments, the instructions cause the processor to perform an embodiment of the method described above.

Another aspect of the technology is directed to a computerized healthcare needs fulfillment system. In some embodiments, the computerized system is designed to receive a prescription script from the computer of a physician prescribing a medical good or service for a patient. In other embodiments, the prescription script is received from the computer of a patient or the computer of a supplier filling the prescription for a patient. The computerized system of some embodiments performs checks to ensure that the prescribed good or service is appropriate for the patient. In some embodiments, the computerized healthcare needs fulfillment system applies a set of heuristics to identify one or more suggested suppliers for filling a patient's prescription. A supplier may be identified by the system as a suggested supplier based on one or more criteria, for example, based on the price charged by the supplier for the prescribed good or service, the proximity of the supplier to the patient, the performance rating of the supplier, the expertise of the supplier, and/or other ancillary services offered by the supplier.

In some embodiments, the healthcare needs fulfillment system facilitates communication with the patient, such as, for example, through coordination with a call center or by transmitting an electronic message directly to the patient, to notify the patient when a better supplier is available for providing the patient's prescribed good or service. In some embodiments, the computerized system determines whether a better supplier exists by comparing the current fulfilling supplier to the one or more suggested suppliers. In some embodiments, if the current fulfilling supplier is not one of the suggested suppliers, then a better supplier exists. In some embodiments, when one or more better suppliers exist, the patient is provided the option of switching to one of the one or more better suppliers. In other embodiments, the computerized system identifies only one suggested supplier and automatically selects said supplier to fill the prescription script for the patient. In various embodiments, the computerized system authorizes the prescription script, transmits the prescription script to the computer of the selected supplier, and receives status updates from the selected supplier's computer.

Another aspect of the disclosure is directed to another method of fulfilling and managing prescriptions. The method of some embodiments includes: receiving a prescription in electronic form, wherein the prescription includes a pharmaceutical drug name and a dosage; receiving patient information in electronic form, wherein the patient information includes an identifier linking a patient to a prescription benefit plan if applicable; accessing a database of drug pricing data comprising current drug prices at a plurality of participating pharmacies; determining a suggested pharmacy based at least in part on the pharmaceutical drug name, the dosage, the prescription benefit plan if applicable, and the current drug pricing data; and sending the electronic prescription to a selected pharmacy for fulfillment.

In some embodiments of the method, the suggested pharmacy is also determined based, at least in part, on the location of the plurality of participating pharmacies. In some embodiments, the suggested pharmacy is automatically chosen to be the selected pharmacy. In other embodiments, identifying a suggested pharmacy includes: identifying a plurality of suggested pharmacy options, providing a list of the suggested pharmacy options to the user in a selectable format, and receiving an input from the user indicating the selected pharmacy. In some embodiments, the plurality of suggested pharmacy options comprises a mail-order option and one or more pharmacies. In some embodiments, the prescription and patient information is provided in electronic form by a user. In some such embodiments, the user is the patient or healthcare provider of the patient. In other embodiments, the prescription and patient information are sent by a user in a non-electronic format, and are later received by the system in electronic format upon uploading by an individual or computer. In some embodiments, the identifier is a patient-specific identification code or username linking the patient to a patient-specific profile, which stores patient-specific information, including at least the patient's: prescription benefit plan, birthdate, name, address, and current prescriptions. The patient-specific profile of some embodiments stores financial account information for the patient. In some such embodiments, the method further includes deducting payment from the financial account information when the electronic prescription is received, adjudicated, or fulfilled by the selected pharmacy.

In some embodiments, the method further includes tracking the electronic prescription and updating a prescription status that is viewable by the user when the selected pharmacy receives the electronic prescription, when the selected pharmacy adjudicates the electronic prescription, and when the selected pharmacy fulfills the electronic prescription.

In some embodiments, the method further includes receiving a question from the patient, identifying a category to which the question pertains, and directing the question to an appropriate resource. In such embodiments, an order status question or a payment question is directed to the selected pharmacy, a benefits question is directed to the patient's pharmacy benefits manager, and a health question is directed to a professional health services representative or healthcare provider.

In some embodiments of the method, the current drug prices are updated periodically to reflect pricing data received from a plurality of participating pharmacies during a bidding process. In such embodiments, the bidding process includes: providing various pharmacies with access to participate in bidding covering a next pricing cycle, and receiving bids for the next pricing cycle from a plurality of participating pharmacies.

Another aspect of the disclosure includes a system for fulfilling and managing prescriptions. The system of various embodiments includes: a receiver configured to receive an electronic prescription and patient information from a user via a web-based interface, wherein the electronic prescription comprises a pharmaceutical drug name and a dosage, and the patient information comprises an identifier linking a patient to a prescription benefit plan if applicable; a database of drug pricing data comprising current drug prices at a plurality of participating pharmacies; a processor configured to determine a suggested pharmacy based at least in part on the pharmaceutical drug name, the dosage, the prescription benefit plan, and the current drug pricing data; and a transmitter configured to send the electronic prescription via a web-based interface to a selected pharmacy for fulfillment.

In some embodiments, the system further includes a memory configured to store a patient-specific profile, which comprises patient-specific information, including at least the patient's: prescription benefit plan, birthdate, name, address, and current prescriptions. In some embodiments, the system further includes a memory configured to store pharmacy-specific information, including at least a name and an address for each pharmacy. In some such embodiments, the memory comprises a web-accessible database.

A further aspect of the disclosure is directed to a method of fulfilling and managing prescriptions. The method includes: receiving a processed claim record from a payer, PBM, or claim aggregator, wherein the processed claim record identifies a fulfilling pharmacy, a prescription drug, a patient, and an address of the patient; generating an eligible claim switch file; sending the eligible claim switch file to a pharmacy evaluator; receiving a report from the pharmacy evaluator identifying a suggested pharmacy, wherein the pharmacy evaluator identifies a suggested pharmacy by evaluating a plurality of pharmacies at least in part on proximity to the patient and price of the prescription drug; determining if the patient is a target patient, wherein a patient is a target patient if the fulfilling pharmacy is not the suggested pharmacy; and sending a list including the target patient to a caller for contacting to determine if the target patient wants to transfer the prescription to the suggested pharmacy.

In some embodiments of the method, the suggested pharmacy includes a plurality of suggested pharmacy options. In some embodiments, the method further includes calling the target patient to determine if the target patient would like to transfer the prescription to the suggested pharmacy.

In some embodiments, the method further includes: receiving a notification from the caller when the target patient authorizes a transfer to a new pharmacy, and contacting the new pharmacy to transfer the prescription for the patient, wherein the new pharmacy is the suggested pharmacy or one of the plurality of suggested pharmacy options. In some embodiments, the pharmacy evaluator is an outside vendor or operated by an outside vendor. Additionally or alternatively, in some embodiments, the pharmacy evaluator is a server or computer. In some embodiments, the caller is an outside vendor or operated by an outside vendor. Additionally or alternatively, in some embodiments, the caller is a person or computer.

Furthermore, an aspect of the disclosure is directed to a system for fulfilling and managing prescriptions in which the system includes: a receiver configured to receive a processed claim record from a payer, PBM, or claim aggregator via a web-based interface, wherein the processed claim record identifies a fulfilling pharmacy, a prescription drug, a patient, and an address of the patient; a processor configured to generate an eligible claim switch file; and a transmitter configured to send the eligible claim switch file to a pharmacy evaluator. In some embodiments, the receiver is further configured to receive a report from the pharmacy evaluator identifying a suggested pharmacy, the processor is further configured to determine if the patient is a target patient (wherein a patient is a target patient if the fulfilling pharmacy is not the suggested pharmacy), and the transmitter is further configured to send a list including the target patient to a caller for contacting to determine if the target patient wants to transfer the prescription to the suggested pharmacy.

These are just some of the system's potential features and functions. Any particular system may have some of or all these features and functions and/or additional or alternative features and functions. The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the systems, methods, devices, and/or processes described herein will become apparent in the teachings that follow.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting.

DETAILED DESCRIPTION OF CERTAIN EMBODIMENTS

Figure 1:
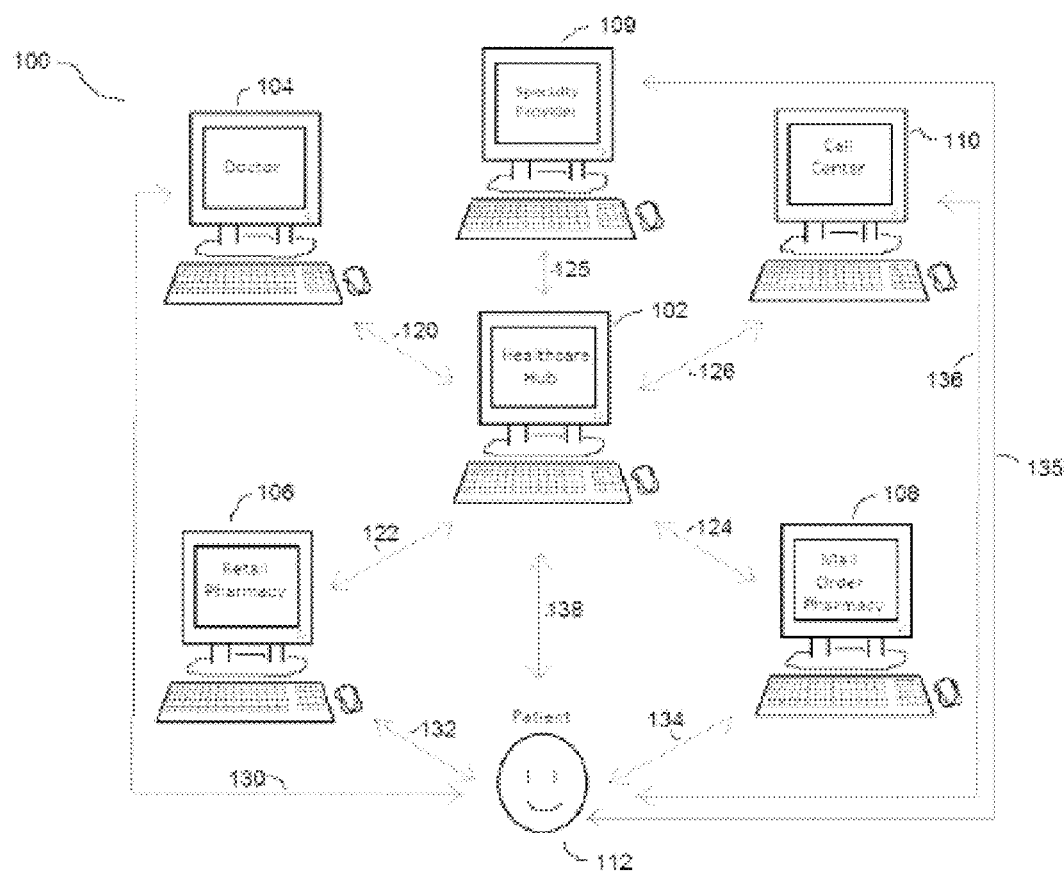
FIG. 1 is a schematic block diagram of one embodiment of a healthcare needs fulfillment system, which depicts the system participants and interactions between the participants.

In the following detailed description, reference is made to the accompanying drawings, which form a part of the present disclosure. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure. For example, a system or apparatus may be implemented or a method may be practiced using any number of the aspects set forth herein. In addition, such a system or apparatus may be implemented or such a method may be practiced using other structure, functionality, or structure and functionality in addition to or other than one or more of the aspects set forth herein.

Similarly, methods disclosed herein may be performed by one or more computer processors configured to execute instructions retrieved from a computer-readable storage medium. A computer-readable storage medium stores information, such as data or instructions, for some interval of time, such that the information can be read by a computer during that interval of time. Examples of computer-readable storage media are memory, such as random access memory (RAM), and storage, such as hard drives, optical discs, flash memory, floppy disks, magnetic tape, paper tape, punch cards, and Zip drives.

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

As used herein, the term "comprising" or "comprises" is intended to mean that the devices, systems, and methods include the recited elements, and may additionally include any other elements. "Consisting essentially of shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

As used herein, a "pharmacy" shall refer to any entity certified as a licensed pharmacy; such licensed pharmacies may include, for example, pharmacies, mail order pharmacies, wholesalers, Central Fill providers, at the like.

As used herein, a "supplier" is an entity that supplies healthcare goods and/or services to patients; the term may refer to, for example, a pharmacy, a provider of biotherapeutics, other specialty therapies, or healthcare services, or a provider of disposable or durable medical goods.

As used herein, "patient" refers to any individual who currently receives or has previously received medical advice and/or treatment. The term shall include any individual who has visited a medical professional and received a prescription for an acute or chronic treatment or medical test.

As used herein, a "prescription," a "prescription script," a "script," and an "Rx" may refer to a written or electronic prescription or recommendation from a healthcare provider for a healthcare good or service.

As used herein, "healthcare goods" include, but are not limited to, pharmaceutical drugs, biologic therapeutics, dietary supplements, vitamins, over-the-counter medications, durable medical equipment, disposable medical supplies, and the like.

As used herein, "healthcare services" include, but are not limited to, laboratory testing, imaging, acupuncture, chiropractic services, and the like.

As used herein, a "user" shall refer to any individual who interacts with, or otherwise uses, any of the systems disclosed herein. For example, a user may be a patient, a patient's guardian or caregiver, a supplier, a healthcare provider, or an employee or contractor of a healthcare provider or healthcare facility.

As used herein, a "patient" may refer to any individual who has used, consumed, and/or purchased healthcare goods or services. The term may refer to a patient or a patient's guardian or caregiver.

As used herein, a "portal" or "central portal" is an entryway to a healthcare needs fulfillment system and may particularly refer to, for example, a graphical user interface through which a user can access and interact with content stored within the healthcare needs fulfillment system. The term may refer to a web-based and/or mobile application dashboard that brings together information from a plurality of sources, organizing and displaying content relevant to a patient's healthcare and facilitating communication between parties important to the patient's healthcare.

For convenience of description and ease of understanding, the discussion and examples provided herein are often directed to systems and methods for fulfilling and managing pharmaceutical prescriptions. However, one of skill in the art will understand that the content of the present application applies equally to other healthcare needs, and all such applications are expressly contemplated and hereby form part of this disclosure. For example, each of the systems and methods described herein may be used for fulfillment and management of orders for any healthcare good or service prescribed or recommended to a patient, such as biologic therapeutics, supplements, vitamins, over-the-counter medications, durable medical goods, disposable medical supplies, laboratory testing, imaging, acupuncture, chiropractic services, and the like.

INTRODUCTION

The systems and methods described herein relate to a total healthcare needs fulfillment system. The healthcare needs fulfillment system of various embodiments is formed of a computer or a network of computers, which provide a central portal to facilitate coordination with parties such as physicians, pharmacies, mail order pharmacies, specialty providers, and patients in order to address all of a patient's healthcare needs, while minimizing the burden on the patient. The healthcare needs fulfillment system of various embodiments is designed to reduce healthcare costs and improve patient care and compliance. In some embodiments, the healthcare needs fulfillment system is particularly designed to reduce the cost of prescription drugs and improve patient adherence to prescribed prescription drug regimens.

Medication usage is commonly differentiated between acute care usage, which is short term (30 days or less) administration to treat immediate illnesses or conditions, and maintenance usage, which is long term (more than 30 days) treatment of chronic illnesses or conditions such as hypertension, high cholesterol levels, arthritis, neurology conditions and the like. Maintenance medication dispensing and usage represents a major healthcare cost (on the order of 75% of prescription costs for many plans), especially due to aging of the American population, and therefore, control of maintenance prescription costs is a principal function of prescription benefit plans and the PBMs that manage them. Dispensing pharmacies are normally of two types: pharmacies (which are local neighborhood businesses where the patient appears in person, can meet with a pharmacist, orders his/her medication, and can usually leave a few minutes later with the dispensed medication in hand) and mail order pharmacies (which are large facilities, usually not open to personal visits from individual patients, but from which a patient's medication order received by mail or through the internet is subsequently filled and dispensed to the patient via mail or courier service).

It is normally recognized by the industry that acute care prescriptions are dispensed primarily by pharmacies, since the patient frequently needs the medication immediately and cannot accept the multiday delay inherent in submitting and dispensing prescription medications from the mail order pharmacies. On the other hand, PBMs commonly urge or even mandate that patients in the plans they administer obtain their maintenance medications from mail order pharmacies. It is a widely held belief that mail order pharmacies have lower operating costs and offer greater discounts available on medication coverage. To the extent that such is the case, use of mail order pharmacies may be a desirable cost control strategy. Moreover, there is some evidence suggesting that mail order pharmacies promote better patient adherence by commonly providing 90-day supplies and delivering directly to a patient's home (resulting in fewer gaps in a patient's ready access to a prescribed medication). Mail order pharmacies often also receive higher quality and safety ratings than pharmacies. However, many patients experience anxiety and/or annoyance when they are forced to use a mail order pharmacy. Numerous studies have established that, for many prescription patients, direct contact with a pharmacist is very important. Professional pharmacists are held in very high regard by patients and their advice is eagerly sought. Most patients are not knowledgeable about medications and a prescribing physician's schedule may not provide sufficient time for a patient to be able to get what he or she believes to be sufficient information from the prescribing physician about all aspects of concern about a prescribed medication. Patients want to be able to speak directly to a skilled health care professional for more information about their medications, especially when a long-term maintenance medication is involved. The prospects for a patient's successful implementation of a medication regimen are enhanced when the patient understands and is comfortable with the medication prescribed. Accordingly, as mail order pharmacies become increasingly utilized and mandated by plans, there is a need for an automated or semi-automated system that can fill the advisory role of a pharmacist. There is utility in providing patients with a user-friendly web-based portal, software application, and/or call center through which patients can learn more about their health conditions and prescribed medications.

Additionally, physicians and other health care providers who write prescriptions often have choices among the different medications they can prescribe for a patient. A physician can, for instance, prescribe a brand name medication or a generic form of that medication, or the physician can choose between two or more different but therapeutically equivalent medication compositions. There are significant differences in cost among the different medication forms, with generic forms normally substantially lower in cost than brand name medications. Even within each group (brand name or generic), there can be substantial cost differences, depending usually on the wholesale prices set by the various manufacturers. Prices can also vary significantly between pharmacies.

It is, thus, extremely difficult for patients, and more generally, patients, to compare prescription drug prices between pharmacies. It is also extremely difficult for patients to compare pharmacies according to other factors such as pharmacy expertise, performance ratings, and/or the appropriateness of substitute or generic medications. As such, most patients are not properly qualified to make assessments about which pharmacy is best for their particular prescription fulfillment. Consequently, needs go unmet and costs are not optimally controlled. Many patients today are unable to optimally select the best pharmacy based on their needs and prescription drug costs.

What would instead be desired is a total fulfillment system, such as any one of the systems described herein. In some embodiments of a total healthcare needs fulfillment system, the pharmacy best suited to fulfill a prescription is the pharmacy that is actually selected to fulfill the prescription. In some embodiments, the system matches pharmacies to the prescription requests that they are best suited to fulfill. This matching may be accomplished in a manner that reduces costs. In some embodiments, the matching process does not rely solely upon pricing/costs to determine which pharmacy is best suited to fulfill each prescription, but also considers factors such as location, plan preferences, pharmacy expertise, and/or pharmacy performance. In some embodiments, this system simplifies prescription ordering services and operates with minimum burden on the patients using the system, while still providing patients with choice.

The system of some embodiments interfaces with both mail order and storefront pharmacies; in other embodiments, the system interfaces exclusively with non-storefront pharmacies. In some embodiments, the system works with dispensers of both brand name and generic medications, and as such, is able to compare cost differences between equivalent medications. For example, in some embodiments, the system may determine if prescription drug substitutions are appropriate, and if so, select a pharmacy that supplies the lowest priced medication, be it generic or brand name, when a physician writes a prescription for a brand name drug. In some embodiments, the system coordinates a bidding process with pharmacies to determine which pharmacies supply the lowest priced medication and/or the best combination of affordable medication and ancillary service offerings.

In some embodiments, the system provides a central portal for a patient to manage and view all of his/her prescriptions in one place, while the system may also divide and send the patient's prescriptions to different pharmacies based on pharmacies' expertise and prices. Such a system may result in more optimal costs and services and permit pharmacies to more efficiently manage their inventories.

The system of some embodiments also provides a central resource which patients and patients can access to ask questions regarding prescription orders, copays, prescription benefits, and their healthcare, health conditions, and general health.

The total fulfillment system of some embodiments provides an online tracking system allowing patients, doctors, and other users of the system to track prescription orders. Such a system may allow users to track when an order has been received by a pharmacy, adjudicated, fulfilled, and shipped. The data from such a system could ideally be used to track prescription ordering histories and to provide data that can be analyzed to determine how to increase prescription fulfillment efficiencies.

System Overview

FIG. 1 is a schematic block diagram of one embodiment of a healthcare needs fulfillment system 100. The diagram depicts the system participants and interactions between the participants. The healthcare needs fulfillment system 100 is operated by the healthcare hub 102. The healthcare hub 102 receives information from, and sends information to, doctors 104, retail pharmacies 106, mail order pharmacies 108, specialty providers 109, call centers 110, and patients 112. (As used herein, "doctor" may refer to a physician, nurse, physician's assistant, or other employee or contractor of a physician.) The patient 102 is also able to interact with each participant in the system, and in some embodiments, the patient 102 exchanges information with the patient's doctor 104, a call center 110, a retail pharmacy 106, a mail order pharmacy 108, a specialty provider 109, and/or the healthcare hub 102. In a preferred embodiment, healthcare needs fulfillment system 100 is, at least in part, a network of communicatively-connected computers and all references to doctors 104, retail pharmacies 106, mail order pharmacies 108, specialty providers 109, call centers 110, and patients 112 refer, specifically, to computers operated by doctors, retail pharmacies, mail order pharmacies, specialty providers, call centers, and patients, respectively. In various embodiments, the healthcare hub 102 is formed of one or more servers or other computers. The healthcare hub 102 of some embodiments is owned, managed, and/or operated by a PBM or other manager of health plans, programs, and/or prescriptions.

The healthcare hub 102 is configured to exchange information with the system participants in order to manage prescription fulfillment. The healthcare hub 102 of various embodiments is configured to achieve one or more of the following objectives: reduce healthcare costs, minimize the burden of prescription management experienced by the patient, ensure that the patient receives the correct prescribed goods or services, and provide an avenue for the patient to receive answers to health and healthcare-related questions. In some embodiments, the healthcare hub 102 achieves one or more of the following objectives through the exchange of information with the system participants. The healthcare hub 102 receives information from a doctor 104 via a communication link 120. This information can include, for example, a prescription (script) for a patient 112 and information about the patient 112. The information about the patient 112 can include, for example, a patient-specific identifier and/or information about a patient's health conditions, prescribed drugs, medical history, height, weight, and/or birthdate. The healthcare hub 102 can transmit information back to the doctor 104 via the communication link 120. In some embodiments, the communication link 120 is a two-way (forward and reverse) communication link. The healthcare hub 102 may, for example, request additional information from the doctor 104. In some embodiments, the healthcare hub 102 requests clarification about whether a prescribed brand name drug can be substituted with a comparable generic drug. The healthcare hub 102 may also contact the doctor 104, for example, to inquire about gaps in care, to communicate best practices in care, to provide tips for managing a patient's disease state, or to alert the doctor 104 that the patient 112 is currently receiving prescriptions that may negatively interact with a prescription newly prescribed by the doctor 104. The communication link 120 of some embodiments includes an internet connection. In other embodiments, the communication link 120 may be a telephonic or facsimile connection.

In some embodiments, once the healthcare hub 102 has received a prescription from a doctor 104 and verified that it is an appropriate prescription, the healthcare hub 102 may transmit the prescription to a retail pharmacy 106, a mail order pharmacy 108, or a specialty provider 109 via communication link 122, communication link 124, or communication link 125, respectively. In some embodiments, the communication links 122, 124, and 125 are two-way (forward and reverse) communication links. The retail pharmacies 106, mail order pharmacies 108, and specialty providers 109 of some embodiments send notifications to the healthcare hub 102 via communication link 122 as a prescription is processed through the respective pharmacy's system. For example, in some embodiments, the retail pharmacy 106 will send notifications to the healthcare hub 102 via the communication link 122 when the prescription order has been received, processed, and filled. This may allow the healthcare hub to generate prescription status updates. Similarly, in some embodiments, the mail order pharmacy 108 and specialty providers send notifications to the healthcare hub 102 via the communication links 124 and 125, respectively, when a prescription order has been received, processed, filled, and if applicable, deducted for in a patient's payment account and/or shipped. Again, this may allow the healthcare hub 102 to generate prescription status updates. Additionally or alternatively, notifications sent to the healthcare hub 102 from the pharmacies 106, 108 and specialty providers 109 provide the healthcare hub 102 with data that it can store, analyze, and/or report regarding the speed, error rate, etc. of the respective pharmacies 106, 108 and specialty providers 109. Such data enables the healthcare hub 102 to evaluate and benchmark pharmacy performance.

In other embodiments, the healthcare hub 102 sends requests for bids related to particular medical goods or services to retail pharmacies 106, mail order pharmacies 108, and/or specialty providers 109 via the respective communication links (122, 124 and/or 125). Additionally or alternatively, in some embodiments, the healthcare hub 102 provides various pharmacies 106, 108 and/or specialty providers 109 with access to a bidding system, such as, for example, by sending an electronic invitation or a link to a bidding website. In response, the retail pharmacies 106 and/or mail order pharmacies 108 may provide bids back to the healthcare hub 102 via the respective communication links (122, 124 and/or 125). In various embodiments, the bids are submitted electronically to the healthcare hub 102 through a web-based portal.

In some embodiments, the communication links 122, 124, and/or 125 may be telephonic or facsimile connections. In a preferred embodiment, one or more of the communication links 122, 124, and 125 are web-based and/or internet-based connections.

In some embodiments, the healthcare hub 102 applies a rule engine, performs calculations, and/or performs comparisons to determine if a prescription is being filled by the best or lowest-priced retail pharmacy 106. If the healthcare hub 102 determines that one or more better options exist, the healthcare hub 102 of some embodiments provides information about the one or more better options to a call center 110 via a communication link 126. In some embodiments, the call center 110 is operated by an outside vendor operating under an agreement with the healthcare hub 102. In other embodiments, the call center 110 is a call center facility, an individual employee, or an automated calling system operated by the healthcare hub 102. In other embodiments, the call center 110 may be a facility, company, individual or computer that communicates with patients electronically via text messaging, emailing, mobile push notifications, or internet-based messaging. The call center 110 of some embodiments initiates a call or other communication with a patient 112 via communication link 136 to determine if the patient 112 would like to switch pharmacies. The call center 110 of some embodiments also provides the patient 112 with additional healthcare tips, prescription reminders, healthcare adherence reminders, and/or other healthcare-related content after receiving such tips, reminders, and content from the healthcare hub 102 via the communication link 126. In some embodiments, the communication link 126 is a two-way (forward and reverse) communication link. For example, in some embodiments, the call center 110 transmits authorization information via communication link 126 back to the healthcare hub 102, indicating whether the patient authorized a pharmacy switch.

In some embodiments, the patient 112 can send patient-specific information, prescriptions received from a doctor 104, and/or healthcare questions to the healthcare hub 102 via communication link 138. The healthcare hub 102 of some embodiments sends prescription status updates to the patient 112 via the same communication link 138. In some embodiments, the healthcare hub 102 provides a web-based interface through which a patient 112 can easily view all of the patient's prescribed medical goods and services-even if several pharmacies and suppliers are providing the various goods and services. In some such embodiments, a patient logged into a web portal can track the status of each prescribed good and service and provide financial information to facilitate the automatic payment of copays. Additionally or alternatively, in some embodiments, the healthcare hub 102 is configured to provide answers to the patient's questions, feedback from a care team, and/or health education content via communication link 138. In some embodiments, the healthcare hub 102 will alert a patient 112 of potential drug interactions, remind a patient to adhere to a healthcare or wellness regimen, alert a patient 112 when healthcare goods or services utilized by the patient 112 are available at a "better pharmacy", and/or provide a patient 112 with educational health and wellness tips. The healthcare hub 102 of some embodiments provides personalized content related to disease states and/or health topics of relevance to a particular patient 112 via communication link 138. In some such embodiments, the content is delivered to the patient in a highly accessible format to empower the patient to make informed health, wellness, and healthcare decisions. For example, in some embodiments, communication link 138 is a wireless communication link, and content is sent from the healthcare hub 102 to the patient 112 via text messaging or email or through a web-based portal or software application. In some embodiments, the healthcare hub 102 may connect the patient 112 directly to a doctor 104, retail pharmacy 106, mail order pharmacy 108, specialty provider 109, or call center 110 in order to have the appropriate party answer the patient's questions. In some such embodiments, the patient 112 exchanges information back and forth with the doctor 104, the retail pharmacy 106, the mail order pharmacy 108, the specialty provider 109, and/or the call center 110 via communication link 130, 132, 134, 135 and 136, respectively.

In some embodiments, the doctor 104, the retail pharmacy 106, the mail order pharmacy 108, the specialty provider 109, the call center 110, and the patient 112 are all connected to the healthcare hub 102 via a network, for example, the Internet. In some embodiments, the patient 112 is also connected to the doctor 104, the retail pharmacy 106, the mail order pharmacy 108, the specialty provider 109, and the call center 110 via a network, such as the Internet. In other embodiments, the patient 112 exchanges information with the doctor 104, the retail pharmacy 106, the mail order pharmacy 108, the specialty provider 19, and/or the call center 110 via a telephonic connection or in-person interaction. Thus, it is to be appreciated that, in at least some embodiments, the communication links 120, 122, 124, 125, 126, 130, 132, 134, 135, 136, and 138 are representative of the communication functionality rather than physical connections.

Figure 2:
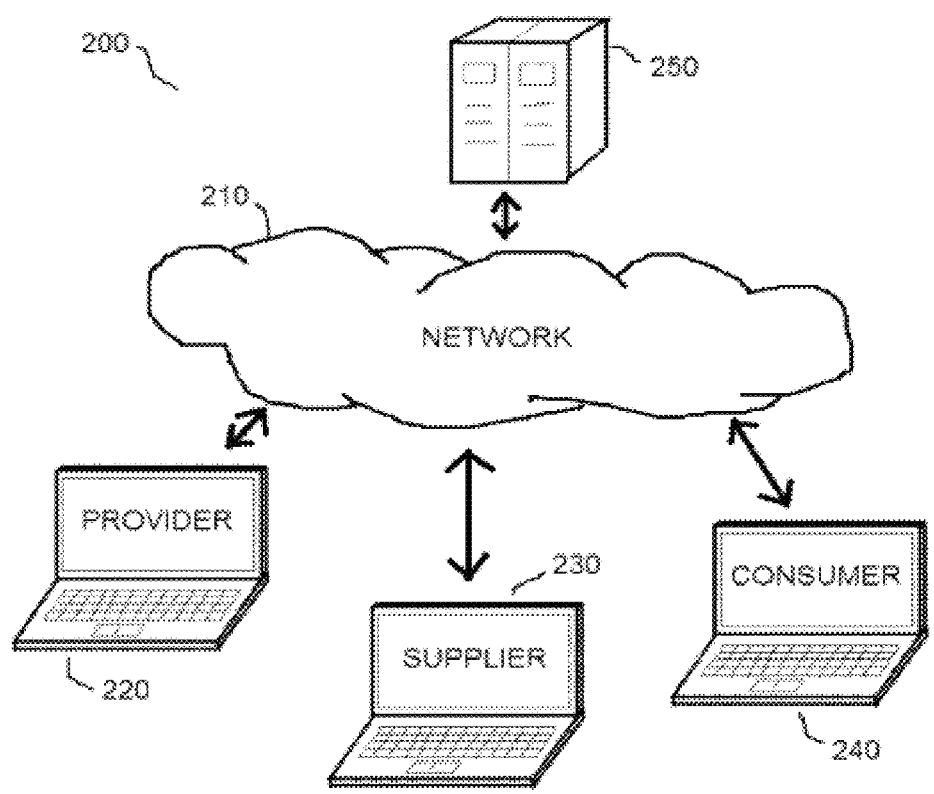
FIG. 2 is a schematic block diagram of one embodiment of a healthcare needs fulfillment system, which depicts the system participants and interactions between the participants.

In another embodiment of a healthcare needs fulfillment system, the system 200 is formed of one or more computers, such as one or more servers 250 coupled via a communication network to at least one or more supplier computers 230, one or more provider computers 220, and one or more patient computers 240. One example of such a system is provided in FIG. 2. Specifically, FIG. 2 illustrates a schematic diagram of the hardware components found in one embodiment of a healthcare needs fulfillment system 200 and includes a schematic illustration of the interactions between said components. One skilled in the art will appreciate that the embodiment is illustrative in nature only and various components may be added, deleted, or substituted and various different hierarchies and modes of communication between the devices may be employed. In the depicted example, the healthcare needs fulfillment system 200 is formed of a plurality of computerized devices. The system 200 includes a communication network 210 through which some or all of the various devices communicate with one another. In some embodiments, a plurality of the devices are configured to transmit information to, and receive information from a server (i.e., the healthcare hub) 250 via the communication network 210. The network can be a local area network (LAN) or a wide area network (WAN). In some embodiments, the network is a wireless communication network to which at least some of the devices are connected, such as, for example, a mobile WiMAX network, LIE network, Wi-Fi network, or other wireless network. In other embodiments, the communication between at least some of the system devices and the server 250 occurs over the Internet via a wired network, such as a DSL cable connection, or over Ethernet or an intranet.

In various embodiments, the system is accessible to users of the system via user workstations, such as provider workstations 220, supplier workstations 230, and patient workstations 240. The workstations may be specialized computers configured solely for connection to the system 200, or they may be generalized computers made to perform specialized functions through its connection to the system 200. For example, in some embodiments, the various workstations 220, 230, and 240 are desktop computers, laptop computers, and/or mobile devices such as tablets, smartphones, or wearable computing devices.

In various embodiments, the healthcare needs fulfillment system 200 is owned, operated, and/or managed by a prescription plan manager, such as, for example, a PBM, or other healthcare plan manager or other manager of prescriptions or healthcare programs. The system may enable a plan manager to better manage a patient's prescribed treatments, improve patients' adherence to healthcare treatments, reduce costs, and improve outcomes. Using the system, a plan manager can easily review all of a patient's prescribed treatments (e.g., prescribed healthcare goods or services) across providers and across suppliers. Regardless of who prescribes the treatment and who supplies the treatment, the list of treatments is available in one readily accessible location. A patient's health profile may also be available within the system. Thus, in such embodiments, plan managers and providers can review a patient's diagnoses and prescribed treatments and identify any treatment gaps, e.g., recommended treatments the patient is not currently receiving. If a treatment gap is identified by the patient's provider, the provider may submit an additional prescription to the system 200. If the treatment gap is identified by the plan manager, the plan manager can utilize the system 200 to contact the patient's provider and recommend the treatment.

Additionally, in various embodiments, the system 200 fills many of the consultative roles previously filled by a retail pharmacy or local supplier. In certain embodiments, the system 200 provides a repository of health-related content and curates it for the patient, such that information helpful to the patient is easily accessible to the patient. Adherence reminders and health suggestions may also be delivered to the patient. The patient may also be able to submit health and treatment-related questions through the system 200 to the plan manager, such that the patient no longer feels a need to visit and speak with a local pharmacist. Advantageously, in some such embodiments, the system 200 acts as an intermediary; with no direct communication between suppliers and patients, the plan manager is able to assign prescriptions to suppliers without regard for patient-supplier relationships; thus, the plan manager achieves more flexibility in sourcing prescriptions. Such a system enables plan managers to send prescriptions to the best supplier for the patient, with "best" being a patient-specific determination that may include variables such as, for example, price, disease-specific expertise, quality ratings, and/or speed of fulfillment. Such a system also enables plan managers to reevaluate suppliers and transfer prescriptions whenever the plan manager deems it to be appropriate.

In certain embodiments, the system 200 also handles all payments automatically by storing a patient's financial account information, calculating copayments, deducting copayments from patients' accounts, and depositing payments into suppliers' accounts, thus further simplifying interactions between patients and suppliers. In some embodiments, efficiency in interactions is further improved through improved adjudication procedures. In some such embodiments, the healthcare hub/server 250 adjudicates a prescription immediately upon receipt from a provider. In such embodiments, the prescription is compared to patient and plan information stored within the server 250 to identify the patient's plan, confirm that the patient is eligible to receive the prescribed treatment under the patient's plan, and confirm that there are no known adverse interactions between the prescribed treatment and other treatments currently being provided to the patient. Such embodiments eliminate the need for suppliers to later submit the prescription for authorization and payment.

In various embodiments, the server 250 includes a processor and memory, and software code is stored in the memory, which, when executed by the processor, causes the system to perform system functions, such as, for example, any of the methods and processes described throughout the disclosure provided herein. In some embodiments, the server 250 includes an application server. In some such embodiments, some software code is stored in the server 250, while additional software code is stored on each other network-connected device (e.g., 220, 230, 240) in the form of a software application. In some such embodiments, "back end" functions such as storing information sets in databases and performing calculations, analyses, and information retrieval is largely performed by, and coded for, within the server 250, while "front end" functions, such as the display of information on a graphical user interface (GUI) and receipt of user inputs, is performed by, and encoded within, the other network-connected devices (220, 230, 240). Additionally or alternatively, in some embodiments, the server 250 includes a web server and various features and functionality are made possible by the software code stored within the server 250. In some such embodiments, each user workstation 220, 230, 240 may include an internet browser, through which users can access, and interact with, the healthcare needs fulfillment system 200. In various embodiments, the server 250 also includes a database server on which information sets such as patient profiles, patient health records, supplier price lists, lists of other supplier metrics, information about various therapies, therapy classifications, known contraindications of therapies, and a repository of content are stored. It will be appreciated to one skilled in the art that the server 250 may be formed of any suitable number of servers. For example, in some embodiments, the server 250 includes one or a plurality of application servers, one or a plurality of web servers, and/or one or a plurality of database servers.

As depicted in FIG. 2, the various devices of the system 200 interact with the network 210, and accordingly, each other, via a two-way (forward and reverse) communication link. The devices each include input/output devices for wired communication connections (e.g., modems, network cards, external data buses, ports, etc.) and/or wireless receivers and transmitters, which allow each device to transmit and receive information. Exemplary information exchanged by the various components is described in more detail below. These are examples only, and various other information exchanges are conceived and expressly contemplated herein.

In certain embodiments, the provider workstation 220 has an input/output device (e.g., mouse, keyboard, touchscreen, monitor, etc.) allowing it to receive inputs from a provider user and display graphical outputs. Users, such as doctors, nurses, nurse practitioners, or employees or contractors of a medical practice or medical facility, may enter prescriptions for patients into the system 200 through the provider workstation 220. In some embodiments, the users of a provider workstation 220 additionally enter a patient's healthcare history, diagnoses, or other information from a patient's medical records into the system 200. Such information is transmitted to the server 250 via the communication network 210 for storage, and optionally, for processing. Users of the provider workstations 220 may also receive requests to verify patient information, authorize a switch for a patient from a brand name healthcare product to a generic equivalent, confirm that a prescription is correct if the system identifies that it is inconsistent with the patient's diagnoses or if a potential adverse reaction is detected with another prescription or an allergy of the patient. Users of the provider workstations 220 may also connect to the system 200 in order to access content about various therapies and other health-related information.

The supplier workstations 230 also have input/output devices (e.g., mouse, keyboard, touchscreen, monitor, etc.) for receiving inputs from users and displaying graphical outputs to users. The workstations 230 may receive requests from the system 200 to submit pricing lists, lists of ancillary services offered, or quality-related information such as, for example, average number of prescriptions filled in a specified time period, average speed for filling prescriptions, etc. Suppliers may be able to submit information relevant to such requests to the system 200 via the supplier workstations 230, and such information may be processed and stored in the server 250. The workstations 230 may also receive requests from the system 200 to participate in competitive bidding processes. Such requests are presented to a user of the supplier workstations 230 via a GUI. Such requests may be in the form of a link that connects users to a competitive bidding interface present within the system. Through the workstations 230, suppliers also receive prescriptions for fulfillment and transmit status updates when the prescriptions have been: received, filled, and shipped. A tracking number may also be transmitted with the status update at the time of shipment. In some embodiments, the suppliers also transmit billing and/or financial account information for storage within the server 250 such that, upon fulfillment or shipment of a prescription, the supplier can receive payment automatically.

In various embodiments, in order for a supplier workstation 230 to join the healthcare needs fulfillment system 200, the supplier must comply with certain minimum service requirements and/or connectivity requirements. As an example, the minimum service requirements may include, but are not limited to, prescription fulfillment within a first specified time period, such as a day, and deliver to a patient within a second specified time period.

Regarding connectivity requirements, in some embodiments, in order to join the system 200, the supplier workstation 230 must download certain software and demonstrate that it is able to successfully receive electronic messages from the healthcare hub/server 250 and reply to such messages. For example, in one embodiment, the supplier workstation 230 much establish connectivity through an HTTP Web Request/Response and format messages with an XML body. In certain embodiments, the reply messages must conform to a specified format to ensure seamless communication within the system. As one example, in some embodiments, the supplier workstation 230 must prove that it is able to receive a new prescription message from the server 250 and identify all data included in the message. In some embodiments, a new prescription message will follow the same or similar format as an Industry ERx Switch New Rx Message or other format commonly used in the industry. The message of various embodiments will include all data elements needed to fill the prescription and may include additional elements. For example, the message may include some or all of: a patient's name, date of birth, gender, shipping address, the name and quantity of the prescribed good or service, the patient's health coverage information such as a group code, BIN number, a prescription drug's PCN, if applicable, a patient's diagnoses and/or known allergies, and information about the transferring pharmacy, if applicable. In certain embodiments, in order to join the system 200, the supplier workstation 230 must also demonstrate that it is able to generate a new prescription number and construct a reply message confirming receipt of the prescription within 60 seconds (or other specified time interval), wherein the reply message includes the new prescription number. In some embodiments, the new prescription number must be unique to any other prescription received by the supplier on that date; the prescription order will remain the same for the life of the prescription. The server 250 of some embodiments will store the prescription number. In some embodiments, the supplier must also demonstrate that it is able to receive a refill request message containing the prescription number, find the original prescription associated with the refill request, respond to the refill request message within a specified time period, and successfully refill the prescription. Additionally, the supplier workstation 230 may be required to demonstrate that it can send status messages for prescription receipt, fulfillment, shipment, and optionally, delivery, as such trigger events occur. The shipment message of some embodiments must include a carrier and tracking number. In various embodiments, upon receipt and processing of the status messages by the server, the status immediately updates within the system and data transmitted to a provider workstation 220 or patient workstation 240 reflects the update. In some embodiments, the supplier workstation 230 must also demonstrate that it has properly encrypted all messages, for example, using an encryption process such as the X509 XML encryption process.

In various embodiments, each patient workstation 240 has one or more input/output devices (e.g., mouse, keyboard, touchscreen, monitor, etc.) for receiving inputs from a patient and/or a patient's parent, guardian, or caregiver and for displaying graphical outputs to such patients. Upon request by a patient through interaction with a GUI, a patient workstation 240 may receive patient-specific prescription information stored in the server 250. Such information may be displayed to the patient for review. For example, the patient may be able to view all of a patient's prescriptions within a single GUI, including prescriptions filled by diverse, unaffiliated suppliers. The displayed information may include, for example, whether a prescription is due for fulfillment, and if so, whether the prescription has been received, fulfilled, and/or shipped by a supplier. In various embodiments, the prescription will be automatically transmitted to a supplier for refill when it is due for refilling. The patient may also be able to view the number of refills remaining in a prescription, the date the prescription will expire, and similar information. The workstations 240 may also receive patient profile information from the server 250, which is displayed to the patient for review and/or editing; the workstations 240 may further transmit patient profile data to the server 250 in order to add to, or update, the stored information. Additionally, in some embodiments, patients are able to access content, such as, for example, health-related articles, quizzes, games, and mobile or web-based software applications from the server 250 through the patient workstation 240. Patients may also be able to transmit questions to the server 250 through the patient workstation 240. Such questions are triaged and transmitted to a supplier, provider, and/or plan manager for response. Additionally or alternatively, in some embodiments, a patient may be able to transmit financial account information via the patient workstation 240 for storage within the server 250, thereby enabling automatic payments to be made when a prescription has been filled, shipped, or delivered.

Figure 3:
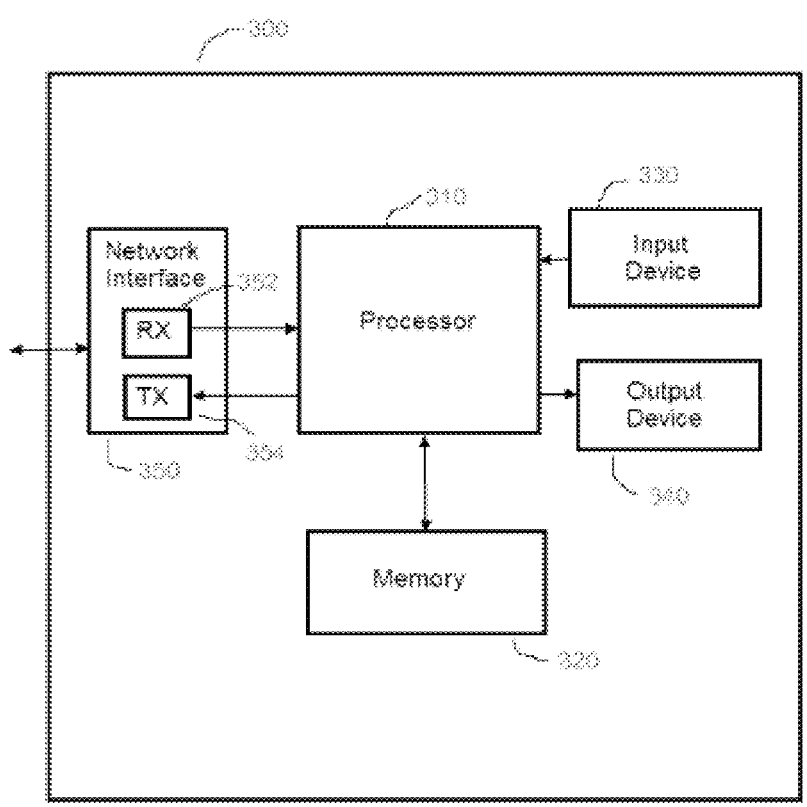
FIG. 3 is a functional block diagram of one embodiment of a healthcare needs fulfillment system.

In another embodiment of the healthcare needs fulfillment system, the system 300 is formed of one or more servers or other back-end computing devices that drive the operations. The server of such embodiments is configured to receive information from, and send information to, various remote components, and is further configured to store data and execute stored instructions, enabling the system to perform some or all of the functions and methods described herein. A functional block diagram of one such embodiment of the healthcare needs fulfillment system is depicted in FIG. 3. Although described separately, it is to be appreciated that functional blocks described with respect to the healthcare needs fulfillment system 300 need not be separate structural elements. For example, the processor 310 and memory 320 may be embodied in a single chip. Similarly, the processor 310 and network interface 350 may be embodied in a single chip. Likewise, the receiver 352 and transmitter 354 may be embodied in a single chip.

The processor 310 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 310 is coupled, via one or more buses, to read information from or write information to the memory 320. The processor may additionally, or in the alternative, contain memory, such as processor registers. The memory 320 can include processor cache, including a multi-level hierarchical cache in which different levels have different capacities and access speeds. The memory 320 can also include random access memory (RAM), other volatile storage devices, or non-volatile storage devices. The storage devices can include hard drives, optical discs, such as compact discs (CDs) or digital video discs (DVDs), flash memory, floppy discs, magnetic tape, and Zip drives.

The processor 310, in conjunction with software stored in the memory 320 executes an operating system, such as, for example, Windows, Mac OS, Unix or Solaris 5.10. The processor 310 also executes software applications stored in the memory 320. For example, the functionality for identifying one or more suggested pharmacies for a patient can be programmed as software stored in the memory 320. In one non-limiting embodiment, the software comprises, for example, Unix Korn shell scripts. In other embodiments, the software can be programs in any suitable programming language known to those skilled in the art, including, for example, C++ and Java.

In one embodiment, the memory 320 may include software for operating the healthcare needs fulfillment system 300 as a web server, such as for example, the software provided by Apache and Tomcat. In one embodiment, the memory 320 includes a web-accessible database, that is, a database which is accessible via the network interface 350. Software stored in the memory 320, such as for example, Oracle 10g, provides database services to the processor 310 and to users of the healthcare needs fulfillment system 300.

The processor 310 is also coupled to an input device 330 and an output device 340 for, respectively, receiving input from and providing output to, a system administrator of the healthcare needs fulfillment system 300. Suitable input devices include, but are not limited to, a keyboard, buttons, keys, switches, a pointing device, a mouse, a joystick, a remote control, an infrared detector, a video camera (possibly coupled with video processing software to, e.g., detect hand gestures or facial gestures), a motion detector, and a microphone (possibly coupled to audio processing software to, e.g., detect voice commands). Suitable output devices include, but are not limited to, visual output devices, including displays and printers, audio output devices, including speakers, headphones, earphones, and alarms, and haptic output devices, including force-feedback game controllers and vibrating devices.

The processor 310 may be further coupled to a network interface 350, including a receiver 352 and a transmitter 354. The transmitter 354, in conjunction with the network interface 350, prepares data generated by the processor 310 for transmission over a communication network according to one or more network standards. The receiver 352, in conjunction with the network interface 350, demodulates data received over a communication network according to one or more network standards. In one embodiment, the transmitter 354 and the receiver 352 are part of the same component, such as, for example, a transceiver. In other embodiments, the transmitter 354 and receiver 52 are two separate components.

Figure 4:
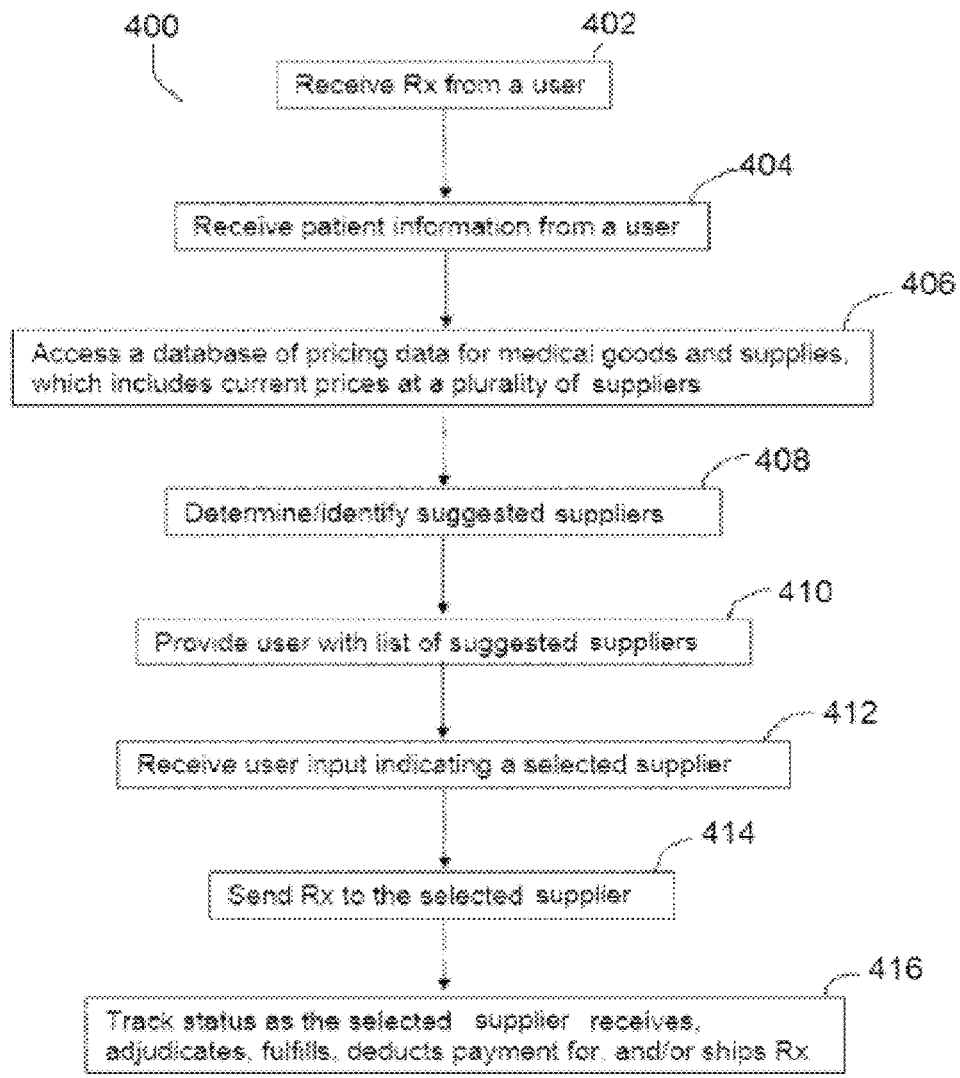
FIG. 4 is a flowchart illustrating one embodiment of a method for fulfilling and managing prescriptions performed by a healthcare needs fulfillment system.

FIG. 4 provides a flowchart illustrating one embodiment of a method 400 for fulfilling and managing prescriptions performed by the healthcare needs fulfillment system 300 of FIG. 3. In the illustrated embodiment, the healthcare needs fulfillment system receives a prescription from a user, as shown in block 402. The prescription includes, at least, the name of a prescription drug or medical good or service and, if applicable, a dosage and/or prescribed frequency of use, as prescribed by a healthcare professional for a patient. In some embodiments, the user submits an electronic prescription to the healthcare needs fulfillment system by logging into a web-based or mobile application interface and entering the electronic prescription into appropriate windows or boxes within the web-based interface. The electronic prescription is transmitted to the healthcare needs fulfillment system over a network connection. In other embodiments, the prescription may be emailed, faxed, or called in to an operator of the healthcare hub. A human or computer affiliated with the healthcare hub can then input the prescription information into the healthcare needs fulfillment system.

In some embodiments, the healthcare needs fulfillment system also receives patient information from a user, as shown in block 404. The patient information may also be entered electronically into a web-based or mobile application interface and transmitted to the healthcare needs fulfillment system via a network. Alternatively, the patient information may be called in, faxed, or emailed to the healthcare hub along with the prescription. The patient information of some embodiments includes, at least, an identifier linking the patient to the patient's respective insurance and/or prescription drug plan. In some embodiments, the identifier simply comprises the patient's name and the group number or member code of the patient's insurance and/or prescription drug plan.

In other embodiments, the identifier is a username or access ID, which uniquely identifies the patient and links the patient to a patient-specific data space within the memory of the healthcare needs fulfillment system. In such embodiments, the patient-specific data space stores data pertaining to a patient-specific profile. The patient-specific profile of some embodiments is maintained by the healthcare needs fulfillment system and accessible by the patient via the web-based or mobile application interface. In some embodiments, the patient-specific profile is editable by the patient and/or the patient's physician. The patient-specific profile of some embodiments includes patient-specific information, including at least the patient's: prescription benefit or other health plan, birthdate, name, address, and current prescriptions. In some embodiments, the patient-specific profile may also include the patient's medical history or other biographical information. In some embodiments in which a patient-specific profile is present, the healthcare needs fulfillment system creates or updates a patient-specific profile upon receiving patient information from a user.

Returning to FIG. 4, after receiving a prescription and patient information from a user, the healthcare needs fulfillment system accesses a database of pricing data for medical goods and services, as indicated by block 406. In some embodiments, the database of pricing data is stored remotely from the healthcare needs fulfillment system and is accessed via a network, such as the Internet. In other embodiments, the database of pricing data is stored within the memory of the healthcare needs fulfillment system. In some embodiments, the database includes listings of current drug prices, listed by drug and by pharmacy. In some embodiments, the database includes listings of current prices for various medical goods and services, listed, for example, by manufacturer, trade name, and supplier. These prices reflect the prices at which each listed supplier has agreed to sell each listed drug or other medical good or service. In some embodiments, the current prices are updated whenever a supplier submits a revised list of prices. In other embodiments, the current prices are updated periodically upon receiving bids from a plurality of bidding suppliers. Such a bidding process is described in more detail below with reference to FIGS. 8A and 8B.

As depicted in block 408, in some embodiments, the healthcare needs fulfillment system identifies one or more suggested pharmacies or other suppliers by evaluating all suppliers listed within the database based, at least in part, on: (1) the prescription product name, and if applicable, the prescribed dosage, prescribed amount, and/or prescribed frequency of use, as identified in the prescription, (2) the patient's prescription benefit plan identified from the patient information, and (3) the current pricing data provided in the database of pricing data for medical goods and services. From this information, the healthcare needs fulfillment system of some embodiments can identify one or more suppliers that will fill the patient's prescription most cheaply.

In other embodiments, the one or more suggested suppliers may be identified taking into account more than just price. For example, in some embodiments, the healthcare needs fulfillment system also takes into account the address of each supplier listed within the database and the address of the patient. The supplier addresses may be stored in a database of supplier information within the memory of the healthcare needs fulfillment system. The patient's address may be stored within the patient-specific profile. In such embodiments, the one or more suggested suppliers identified by the system may include, for example, the three suppliers that will fill the prescription most cheaply within a 3-mile radius of the patient. In other embodiments, the system may be configured to identify a different number of suggested suppliers and/or use a different distance/radius in its calculations. In some embodiments, the healthcare needs fulfillment system additionally or alternatively takes into account other data stored within the database of supplier information when identifying one or more suggested suppliers. For example, in some embodiments, the healthcare needs fulfillment system identifies suggested suppliers based, at least in part, on the expertise, historical performance, and/or quality rating of each supplier. In some embodiments, the healthcare needs fulfillment system monitors and stores metrics indicative of performance as suppliers use the system. For example, in some embodiments, the system monitors and stores the length of time it takes a supplier to fill a prescription, the number of errors or issues that arise, the percent of patients that report adherence to treatment, improved health, satisfaction with their supplier etc. In some embodiments, the healthcare needs fulfillment system takes into account a patient's diagnoses and/or all of a patient's prescriptions, as a bundled package, when evaluating suppliers based on criteria such as price, location, availability, quality, and/or expertise. In this manner, the system may identify one or more suggested suppliers best aligned for managing a patient's conditions and all of a patient's prescribed healthcare needs.

In some embodiments, the healthcare needs fulfillment system provides the user with a list of suggested suppliers, as shown in block 410, and receives a user input, as shown in block 412, indicating which suggested supplier the user has selected to be the patient's new supplier. The list may be transmitted to the user over the Internet and displayed to the user via the web-based or mobile application interface. Similarly, using the web-based or application interface, the user can provide an input to select the new supplier. In some embodiments, only retail pharmacies and/or specialty providers are shown in the list of suggested suppliers. In other embodiments, mail-order is included as one of the user's options in the list of suggested suppliers. Upon receiving the user's input identifying the suggested supplier selected to be the patient's new supplier, the prescription is sent in electronic form to the selected new supplier, as shown in block 414.

In some embodiments of a method for fulfilling and managing prescriptions performed by a healthcare needs fulfillment system, the operations disclosed in blocks 410 and 412 are not included. In such embodiments, after receiving a prescription and patient information from a user and accessing a database of pricing data for prescription drugs and/or other medical goods or services, the healthcare needs fulfillment system identifies one suggested supplier at block 408. As described above, the suggested supplier determination may be based on a supplier's price for a particular good or service, proximity to the patient, particular expertise, speed of fulfillment, availability of the good or service, quality rating, overall price or quality for a bundle of prescriptions, and/or other factors. Once the suggested supplier is identified, the prescription is sent electronically to that supplier.

In some embodiments, the method for fulfilling and managing prescriptions further includes tracking the status of the prescription through the pipeline. That is, in some embodiments, the status of the prescription can be tracked electronically as the selected supplier receives, fulfills, bills for, and/or ships the prescription. Such an operation is shown at block 416. If the selected supplier is a mail order supplier, the healthcare needs fulfillment system may additionally be able to track the status of the shipping process from drop off to delivery. In some embodiments, the selected supplier provides notifications to the healthcare needs fulfillment system when the status of the prescription has changed, thereby allowing the healthcare needs fulfillment system to track the status of the prescription. In some embodiments, the status of the prescription is viewable by the user through the web-based or mobile application interface.

Figure 5:
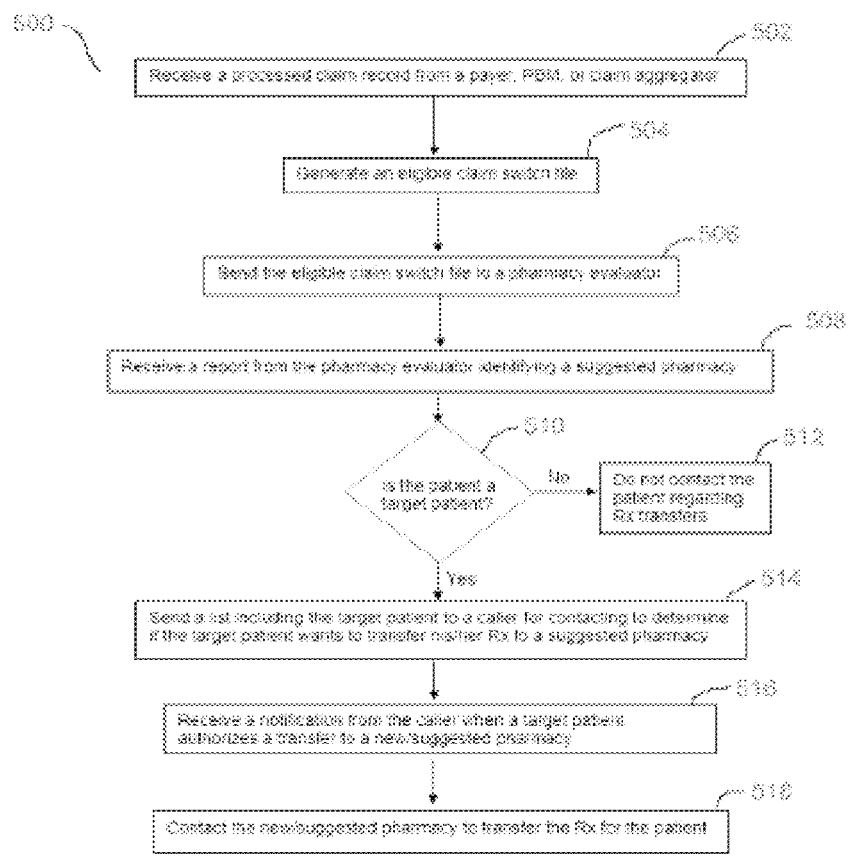
FIG. 5 is a flowchart illustrating another embodiment of a method for fulfilling and managing prescriptions performed by a healthcare needs fulfillment system.

FIG. 5 provides a flowchart illustrating another embodiment of a method for fulfilling and managing prescriptions. In the depicted method 500, the healthcare needs fulfillment system receives a processed claim record from a payer, PBM, or claim aggregator at block 502. The processed claim record includes information about at least one prescription fulfilled at a pharmacy. The processed claim record at least identifies the fulfilling pharmacy, the patient, and the prescribed good or service for each fulfilled prescription. From this information, and optionally, from additional patient information stored in a patient-specific profile, the healthcare needs fulfillment system generates an eligible claim switch file as shown at block 504. The eligible claim switch file identifies one or more prescriptions that may be good candidates for transfer to another pharmacy.

At block 506, the eligible claim switch file is sent to a pharmacy evaluator. The pharmacy evaluator of some embodiments is an outside vendor. In some embodiments, the eligible claim switch file is sent to the pharmacy evaluator via the web-based or mobile application interface. In other embodiments, the pharmacy evaluator is a sub-system of the healthcare needs fulfillment system, and the eligible claim switch file is sent to the pharmacy evaluator via a LAN, intranet, or electronic connection. The pharmacy evaluator generates a report identifying one or more suggested pharmacies. The one or more suggested pharmacies are pharmacies that would fulfill the prescription most optimally, as determined by taking into account one or more factors. Such factors may include, for example, a pharmacy's pricing, proximity to the patient, particular expertise, speed of fulfillment, availability of the good or service, quality rating, and/or performance rating. At block 508, the healthcare needs fulfillment system receives the report from the pharmacy evaluator identifying one or more suggested pharmacies.

At block 510, the healthcare needs fulfillment system evaluates whether the patient is a target patient. In various embodiments, the patient is found to be a target patient if the fulfilling pharmacy listed in the processed claim record is not listed within the report of suggested pharmacies. Such a finding indicates that the patient's prescription is not currently being filled optimally. For example, such a finding may suggest that one or more pharmacies are closer to the patient, cheaper for the patient, have more expertise with a particular health condition of the patient, and/or are better able to manage a patient's entire bundle of prescriptions than the patient's current pharmacy. In some embodiments, additional considerations are taken into account when determining whether a patient qualifies as a target patient. For example, in some embodiments, the healthcare needs fulfillment system determines whether the patient is permitted to transfer prescriptions under the patient's prescription benefit plan. In one example, the healthcare needs fulfillment system excludes all Medicare Part D recipients from the target patient population.

As shown at block 512, if the patient is not identified as a target patient, the patient will not be contacted to discuss a prescription transfer and the patient's prescriptions will not be transferred. If the patient is identified as a target patient, as in block 514, the patient will be included within a list of target patients that the healthcare needs fulfillment system sends to a caller. The list will include, at least, the patient's name, the patient's contact information, the patient's prescription, and the one or more suggested pharmacies. In some embodiments, the caller is an outside vendor contracted to make calls for the healthcare needs fulfillment system. In some such embodiments, the list of target patients is provided to the caller via a web-based or application interface. In other embodiments, the caller is an automated calling sub-system, which forms part of the healthcare needs fulfillment system. The list of target patients may be provided to the sub-system, for example, via a LAN, intranet, or electronic connection. In some embodiments, the caller contacts each target patient included on the list to determine if each target patient would like to transfer the patient's respective prescription to one of the suggested pharmacies. The caller may contact each target patient via phone, email, text-message, push notification, or mail. In some embodiments, the caller provides the target patient with the location and/or the required copay associated with each of the suggested pharmacies to better inform the patient's decision.

In some embodiments of the method, the healthcare needs fulfillment system receives a notification from the caller when a target patient authorizes a transfer of the patient's prescription to one of the suggested pharmacies, as shown at block 516. The healthcare needs fulfillment system contacts the pharmacy selected by the target patient and transfers the prescription for the patient, as shown at block 518. Conversely, in other embodiments, when a target patient in contact with the caller authorizes a prescription transfer, the target patient is instructed to bring the prescription to the selected pharmacy. In other embodiments, when a target patient in contact with the caller authorizes a prescription transfer, the caller contacts the selected pharmacy and transfers the prescription for the patient.

Figure 6:
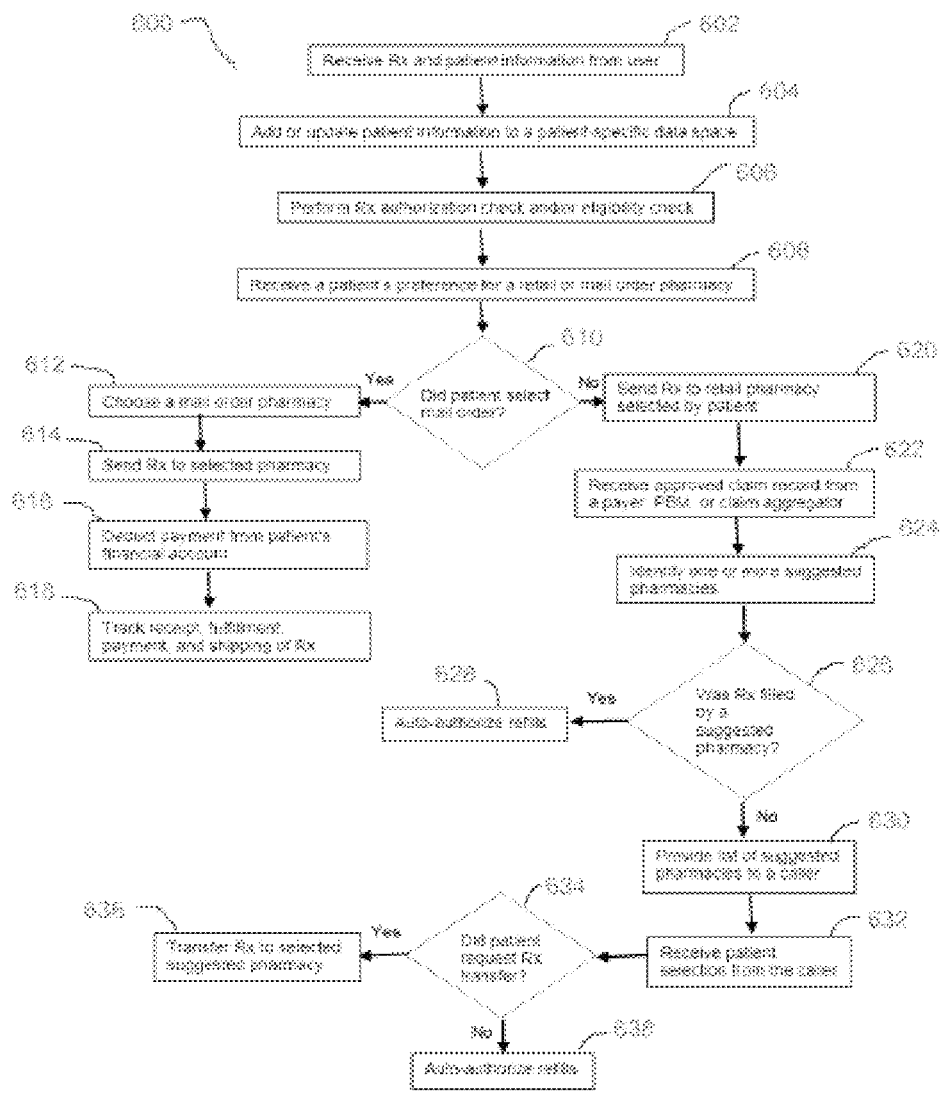
FIG. 6 is a flowchart illustrating another embodiment of a method for fulfilling and managing prescriptions performed by a healthcare needs fulfillment system.

FIG. 6 is a flowchart illustrating another embodiment of a method for fulfilling and managing prescriptions. In the method 600 of FIG. 6, the healthcare needs fulfillment system receives prescription and patient information from a user, as described above in the description of FIG. 4. Upon receiving the information at block 602, the healthcare needs fulfillment system updates a patient-specific profile to include at least some of the information received at block 602. As shown at block 604, if a patient-specific profile does not yet exist for a particular patient, the healthcare needs fulfillment system of some embodiments will generate a patient-specific profile upon receiving patient information from the user.

At block 606, the healthcare needs fulfillment system performs a prescription authorization and/or eligibility check. In some embodiments, the authorization check includes comparing the received prescription to the patient information to determine, for example, whether the prescribed good or service, and dosage or frequency of use, if applicable, is consistent with the patient's diagnosis and/or whether the prescribed good or service might cause adverse effects with other prescriptions of the patient. In some embodiments, the eligibility check includes verifying the patient's insurance or prescription benefits plan and/or determining whether the prescribed good or service is covered by the patient's plan. Additionally or alternatively, in some embodiments, where applicable, the authorization check includes contacting the patient's physician to determine whether a generic drug is an acceptable substitute for a brand name drug. The prescription authorization check of some embodiments is fully automated. In other embodiments, at least a portion of the prescription authorization check is performed by a healthcare needs fulfillment system administrator.

At optional block 608, the healthcare needs fulfillment system receives a patient's preference for mail-order or a particular retail pharmacy. Upon receiving the preference, the healthcare needs fulfillment system processes the preference at block 610.

If the patient selected to receive the prescription via mail order, or if optional block 608 is not present in the system, the healthcare needs fulfillment system choses a mail-order pharmacy or other supplier to be the provider of the prescription, as shown at block 612. The chosen mail-order supplier may be selected at least in part via a bidding system, as described in detail below with reference to FIGS. 8A and 8B. Additionally, or in the alternative, the chosen mail-order supplier may be selected through an evaluation process which weighs one or more criteria such as, for example, the prescription sales prices, quality ratings, safety ratings, and expertise of various suppliers. At block 614, the healthcare needs fulfillment system sends the prescription to the selected mail-order supplier.

Optionally, in some embodiments, the healthcare needs fulfillment system deducts payment for the prescription copay from the patient's bank account (or charges the payment to the patient's credit card) as shown at block 616. To make the operation shown at block 616 possible, a patient's financial account information must be stored in the patient-specific profile. In some embodiments, a patient can add or modify financial account information and/or other patient information included in the patient-specific profile at any time via the web-based interface.

In some embodiments, the healthcare needs fulfillment system tracks the receipt, fulfillment, payment, and/or shipment of the prescription by the mail order pharmacy or other supplier, as shown at block 618. The healthcare needs fulfillment system of such embodiments provides prescription status updates, which the patient or other user of the system can access.

If, at block 610, the healthcare needs fulfillment system determined that the patient selected a particular retail pharmacy, the method proceeds to block 620, and the prescription is sent to the retail pharmacy selected by the patient for fulfillment. Upon receiving an approved claim record from a payer, PBM, or claim aggregator (see block 622), a method similar to the method embodied in FIG. 5 is performed. At blocks 624 and 626, the healthcare needs fulfillment system determines whether the prescription was filled by the best pharmacy for the patient. This determination is performed by identifying one or more "best" or suggested pharmacies, based on factors such as price, proximity to the patient, availability of the prescribed good or service, speed of fulfillment, pharmacy performance, and/or pharmacy expertise and comparing the patient-selected pharmacy to the identified best pharmacies. As described previously, in some embodiments, an outside vendor identifies one or more suggested pharmacies for filling the patient's prescription. The healthcare needs fulfillment system then determines whether the prescription was filled by the best pharmacy for the patient by evaluating whether the patient-selected pharmacy is included in the vendor's list of one or more suggested pharmacies.

In some embodiments, if it is determined that the prescription was filled by one of the best or suggested pharmacies, the healthcare needs fulfillment system will auto-authorize refills of the prescription by the current pharmacy in the future (as shown at block 628). If, on the other hand, it is determined that the prescription was not filled by one of the best or suggested pharmacies, the method proceeds to block 630. In some embodiments, a list of suggested or better pharmacies is provided to a caller. As before, the caller may be a person or a computerized system, and the caller may be an outside vendor or a subsystem of the healthcare needs fulfillment system. In some embodiments, after the caller contacts the patient (via phone, fax, email, text, push notification, etc.) and receives a response from the patient, the response is forwarded to the healthcare needs fulfillment system. At block 632, the system receives the patient's response from the caller. At block 634, the healthcare needs fulfillment system analyzes the patient's response to determine whether the patient requested a prescription transfer to a new pharmacy. As shown at block 636, if the patient requested a transfer, the healthcare needs fulfillment system of some embodiments transfers the prescription to the new pharmacy. In some embodiments, if the patient does not request a transfer, the healthcare needs fulfillment system will auto-authorize refills of the prescription by the current pharmacy in the future (as shown at block 638).

Figure 7:
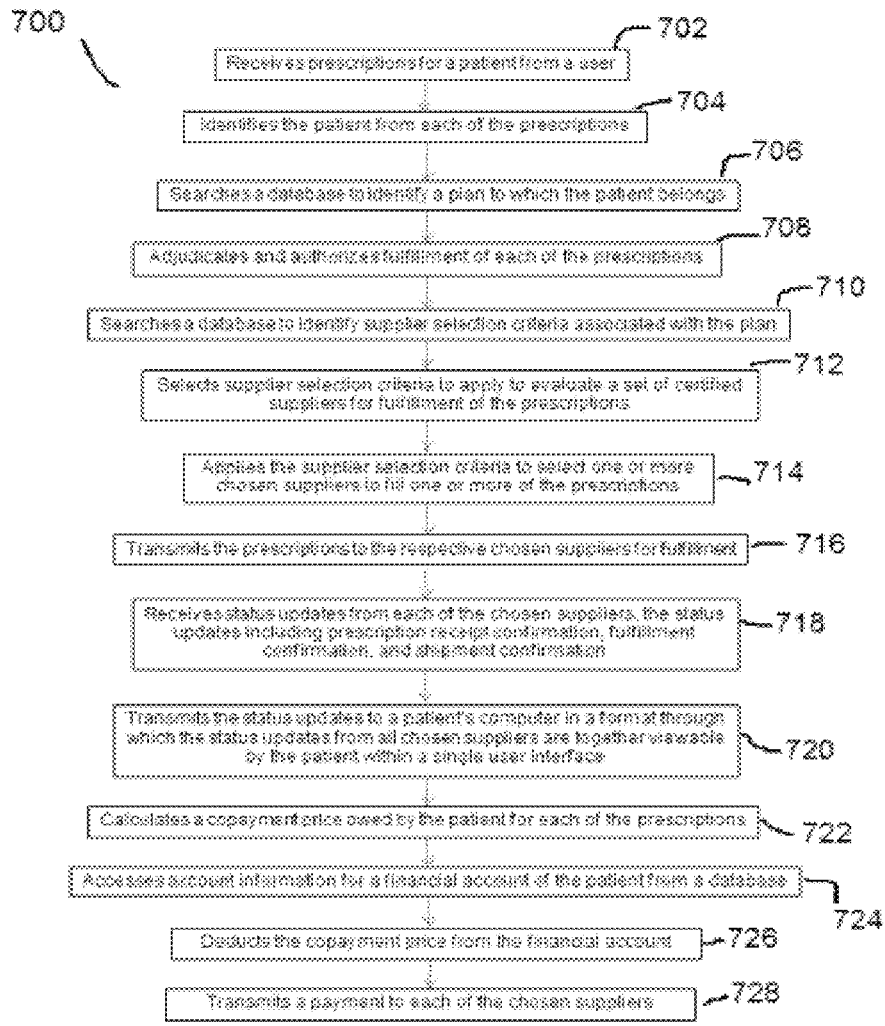
FIG. 7 is a flowchart illustrating another embodiment of a method for fulfilling and managing prescriptions performed by a healthcare needs fulfillment system.

FIG. 7 depicts another embodiment of a method performed by a healthcare needs fulfillment system to fulfill and manage patient prescriptions. In some embodiments, the method 700 is implemented by a healthcare hub, which may be, for example, a computer that is owned, managed, and or controlled by a plan manager and programmed to concurrently manage prescriptions for a multitude of patients. In the embodiment of FIG. 7, the computer implementing the method 700 receives prescriptions for a patient from one or more users' computers at block 702. The prescriptions may be received, for example, from the patient's computer and/or a provider's computer. Each of the prescriptions identifies the patient and a prescribed treatment. At block 704, the computer identifies the patient from each prescription, for example, by locating patient identifying information on the prescriptions. At block 706, the computer searches an internal or external database to identify a plan to which the particular patient belongs. At block 708, the computer adjudicates the prescription and performs prior authorization for fulfillment. For example, in some embodiments, the computer confirms that the patient is eligible for each prescribed healthcare good or service and verifies that the patient's plan covers the prescribed good or service. Such verification may again require looking up required plan coverage data within an internal or external database. At block 710, the computer searches a database maintained by the plan manager to identify supplier selection criteria associated with the patient's plan. The supplier selection criteria may vary with each plan or each plan payer, or the same criteria for selection may be used across all plans. The selection criteria may also vary with each healthcare good or service. Such criteria are described elsewhere herein and may include, for example, a preference to select the supplier offering: the lowest price; the lowest price among suppliers with a certain quality rating; the lowest price among suppliers identified as having an expertise with a particular health condition; the lowest price among suppliers offering a particular ancillary service, the greatest number of ancillary services and the prescribed good or service at the lowest price; or the lowest price among a limited set of suppliers preferred by the plan payer.

At blocks 712 and 714 of the depicted embodiment, the computer selects and applies supplier selection criteria in order to select one or more suppliers to fill one or more of the patient's prescriptions. At block 716, the prescriptions are transmitted to the chosen suppliers for fulfillment. Advantageously, in some embodiments, the prescriptions are transmitted with pre-approval/prior authorization such that the chosen suppliers do not need to later seek authorization to fill the prescriptions. Instead, the chosen suppliers begin fulfillment of the prescription and send status updates to the computer as updating events occur. For example, as shown at block 718, the computer receives prescription receipt confirmations, fulfillment confirmations, and shipment confirmations from each of the chosen suppliers, upon completion of each step. In some embodiments, the computer also receives delivery confirmation when delivery to a patient has been completed. At block 720, the computer transmits the status updates to a patient or related user's computer. In various embodiments, the status updates are transmitted in a format through which updates from all chosen suppliers are together viewable by the patient or related user within a single user interface. For example, in some embodiments, the status updates are displayed on or accessible from a single page within a web-based or mobile application.

In some embodiments, the computer also calculates a copayment price owed by the patient for each of the patient's prescriptions, as shown at block 722. In some such embodiments, the computer accesses account information for a financial account of the patient from an internal database (block 724), deducts the copayment price from the financial account (block 726), and transmits a payment to each of the chosen suppliers (block 728). In some embodiments, the payment is transmitted by the computer along with a plan payer's portion of the payment. Advantageously, in some such embodiments, all information and payments a supplier needs are received from the healthcare hub rather than from the patient.

Figure 8A:
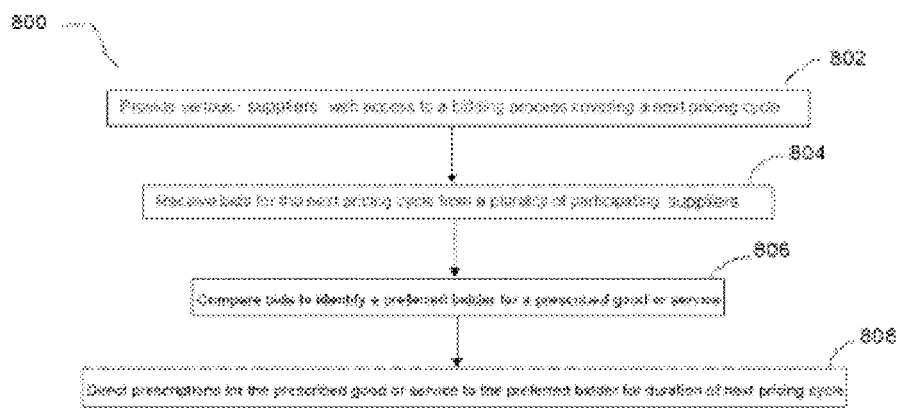
FIG. 8A is a flowchart illustrating an embodiment of a method for identifying a supplier of a pharmaceutical drug, the method performed by a healthcare needs fulfillment system.

FIG. 8A is a flowchart illustrating an embodiment of a method performed by a healthcare needs fulfillment system for identifying preferred suppliers and fulfilling prescriptions using said preferred suppliers. In the illustrated embodiment of the method 800, the healthcare needs fulfillment system employs a bidding process to help identify the preferred suppliers. For example, in block 802, the healthcare needs fulfillment system provides various suppliers with access to the bidding process covering a next pricing cycle. In some embodiments, the prices are set quarterly, so the next pricing cycle is equivalent to the next fiscal or calendar quarter. In other embodiments, other pricing cycles are used, such as, for example, daily, weekly, monthly or annually. In various embodiments, access may be provided to certified suppliers via an electronic link received by email or through a web-based or application interface. Certified suppliers may include suppliers that have met certain service and connectivity requirements, such as those described above with reference to FIG. 2. The certified suppliers may choose whether to participate in the bidding process and become "participating suppliers." To participate in the bidding process, in some embodiments, certified suppliers must follow the electronic link to a secure bidding interface, which may be web-based or software application-based. In other embodiments, the electronic link directs certified suppliers to a downloadable file in which suppliers can enter their bids and return to a healthcare hub/plan manager through a web-based or application interface or via an electronic message such as email.

At block 804, the healthcare needs fulfillment system receives completed bids for the next pricing cycle from a plurality of participating suppliers. Each completed bid includes, at least, the price the respective supplier will charge for each prescribed good or service. In some embodiments, the completed bids additionally include the price the supplier will charge for each formulation and dosage, if applicable, and/or price variations the supplier will charge based on a patient's pharmacy benefits plan. In some embodiments, bids are submitted on a per unit basis. For example, in some embodiments, all bids for medical goods and services are listed as: per tablet, per capsule, per test strip, per MRI, per X-ray, etc. In some such embodiments, the per unit basis is the only price the healthcare needs fulfillment system will consider. Accordingly, in such embodiments, each bidder must sum up all costs they wish to be reimbursed for, such as, for example, the wholesale cost of the good or service, shipping costs, dispensing fees, etc., then perform division to determine the cost per unit. By requiring all bids to be submitted on a per unit basis, the healthcare needs fulfillment system is able to easily and efficiently compare costs across suppliers. Additionally, in some embodiments, participating suppliers may be able to list ancillary services they are willing to provide patients along with the prescription fulfillment.

At block 806, the healthcare needs fulfillment system compares the completed bids to identify the preferred supplier for each good or service, and in some embodiments, for each formulation, each dosage or size, and/or each pharmacy benefits plan or other health plan. As in other embodiments, the preferred supplier may be selected based on various factors, such as, for example, a supplier's prices, fulfillment speed, quality, error rates, and expertise. Information related to one or more of the above-listed factors or other factors may need to be provided by suppliers during the bidding process. In some embodiments, some of the above-listed factors may be collected and stored automatically by the system during use. In some embodiments, the bidding is an open process, allowing the participating suppliers to view the bids of their competitors. In some such embodiments, the bidding is iterative, allowing participating suppliers to submit multiple bids for each healthcare good or service during the duration of the biding process. In other embodiments, the bidding is a semi-open process, allowing the participating suppliers to view the lowest-priced bid or other top bid at any particular point during the bidding process. In some such embodiments, the top bid is displayed with information identifying the supplier that submitted the bid; in other embodiments, the top bid is displayed without identifying information. In still other embodiments, the bidding is closed such that suppliers cannot view the bids of their competitors. In some such embodiments, the bidding is not iterative. At block 808, the healthcare needs fulfillment system directs prescriptions for particular a particular good or service to the respective preferred supplier for the duration of the next pricing cycle. In some embodiments, the system directs new prescriptions received during the next pricing cycle to the respective preferred supplier. In some such embodiments, each prescription remains with its assigned supplier and continues to be filled according to the terms of the supplier's bid submission until the prescription expires, for example, for an entire year or for the lifetime of the prescription.

In some embodiments, participating suppliers may choose which healthcare goods and services they submit bids for. In some such embodiments, there may be healthcare goods or services that do not receive any bids. Additionally, in various embodiments, the bidding process may result in a tie for the top bid. In embodiments in which there is no single preferred supplier or bid winner, one of a plurality of processes may be implemented to assign new prescriptions to a supplier for fulfillment. In some embodiments, patient-specific bundling occurs wherein the prescription is transmitted to a certified supplier that has been selected through the bidding process to fill one or more additional prescriptions for the patient. In such embodiments, the selected supplier is a certified supplier that has submitted the winning bid or bids for one or more additional healthcare goods or services prescribed to the patient. In other embodiments, the prescription is transmitted to a certified supplier identified as having an expertise in a health condition associated with the prescribed healthcare good or service. In other embodiments, the prescription may be transmitted to a certified supplier randomly. In other embodiments, prescriptions for healthcare goods and services having no winning bidder may be sequentially assigned to a rotation of certified suppliers. In other embodiments, the system may bundle a plurality of goods or services without winning bids together to form bundled packages; the system may then provide a link to the certified suppliers to bid on the bundled packages. The prescription may then be transmitted to the supplier that submits a winning bid on the bundled package that includes the prescribed healthcare good or service.

Figure 8B:
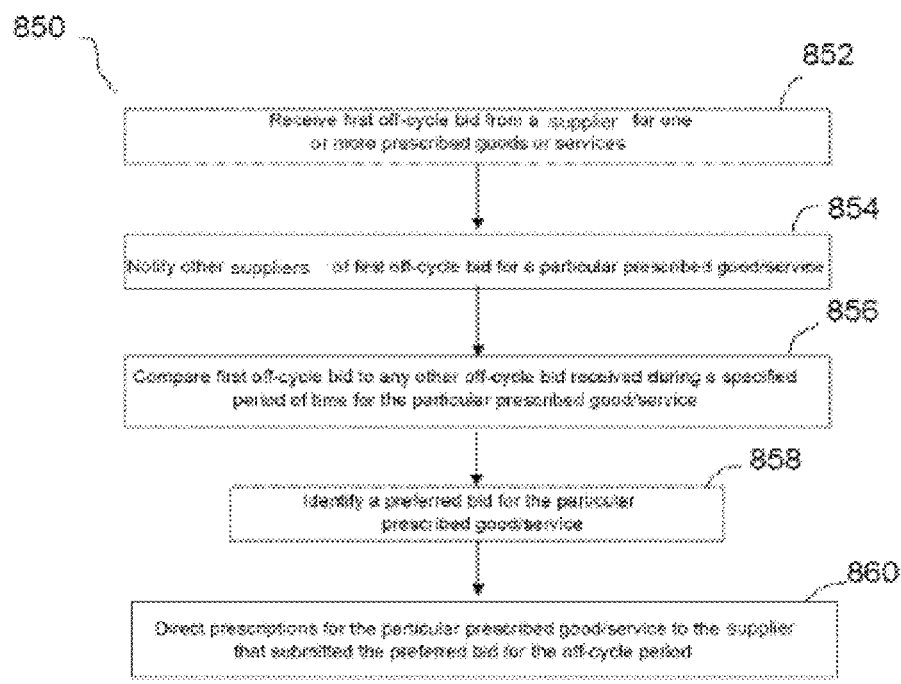
FIG. 8B is a flowchart illustrating another embodiment of a method for identifying a supplier of a pharmaceutical drug, the method performed by a healthcare needs fulfillment system.

FIG. 8B is a flowchart illustrating another embodiment of a method for identifying a preferred supplier of a prescribed good or service through a bidding process. The method 850 of FIG. 8B may be performed by a healthcare needs fulfillment system independently or in conjunction with the bidding process depicted in FIG. 8A. The bidding process of FIG. 8B enables suppliers to offer deals for a period of time that is shorter than the regular pricing cycle. For example, the suppliers may offer "deals of the day" or "deals of the week." In the embodiment of FIG. 8B, the healthcare needs fulfillment system receives a first off-cycle bid from a supplier for one or more medical goods or services, as shown at block 852. The bid may apply to all formulations, dosages, sizes, and pharmacy benefits plans, or the bid may specify the limitations of the bid. At block 854, the healthcare needs fulfillment system notifies other suppliers of the first off-cycle bid received. The notice may be sent directly to the suppliers, such as for example, by mail, phone, fax, push notification, or email, or the notice may be posted in the web-based or application interface. In some embodiments, the other suppliers are provided with a window of time within which they can submit counter-bids. At block 856, the healthcare needs fulfillment system compares the first off-cycle bid to any other bids received during the specified period of time. At block 858, the healthcare needs fulfillment system identifies the preferred off-cycle bid. The preferred bid may be selected based on lowest price alone or on a plurality of factors, such as the factors discussed above. For the specified off-cycle period of time, prescriptions will be directed to the supplier that submitted the preferred bid for a particular good or service, as in block 860.

Figure 9:
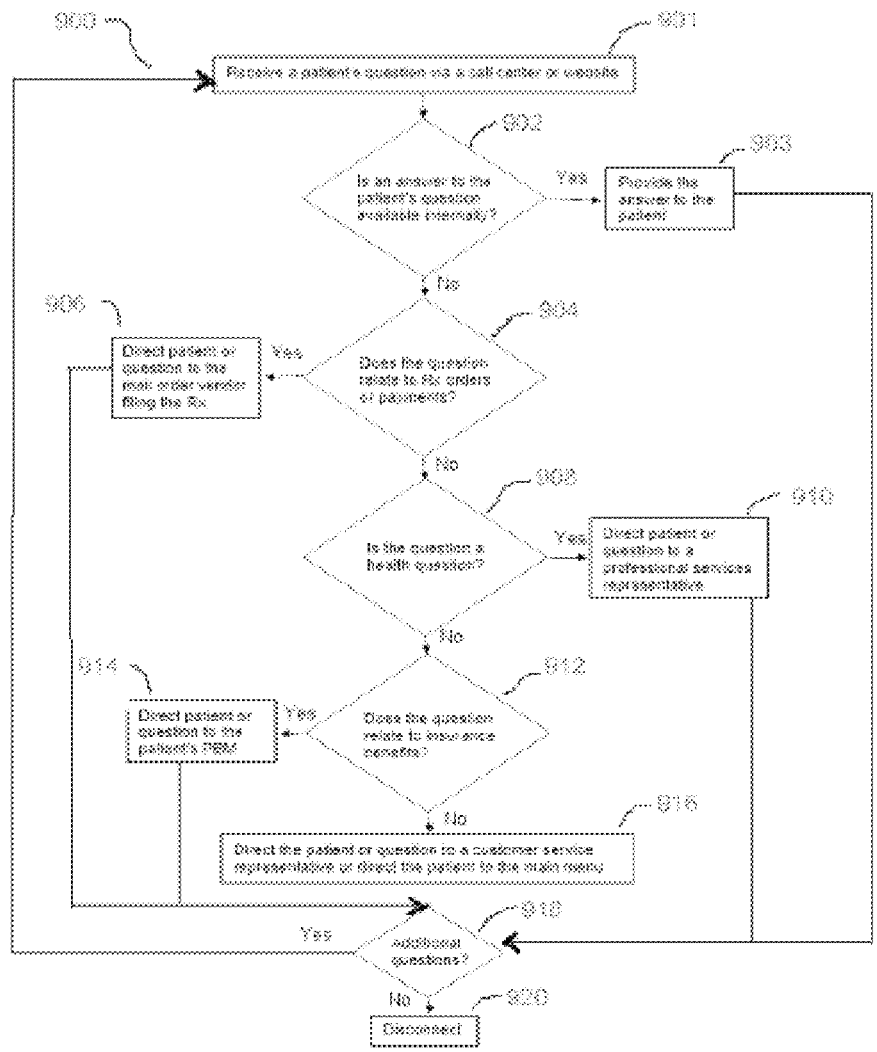
FIG. 9 is a flowchart illustrating an embodiment of a method for answering patients' questions, the method performed by a healthcare needs fulfillment system.

FIG. 9 is a flowchart illustrating an embodiment of a method for answering patients' questions. The method 900 of various embodiments is performed by a healthcare needs fulfillment system. The method 900 can be combined with and/or performed in concert with any of the methods for fulfilling and managing prescriptions described above. As shown at block 901, the healthcare needs fulfillment system of some embodiments receives patient questions through the web-based or application interface or via an email, text message, or a call center. In some embodiments, the operator of the healthcare needs fulfillment system may have the capability of answering some questions directly. In such embodiments, optional block 802 may be performed. At block 802, the system determines whether an answer to a patient's question is readily available onsite. If so, it is answered at block 803. If no, or if optional block 802 is skipped, the patient's question is triaged and the general topic determined in order to direct the question to the most applicable provider of information. In some embodiments, the healthcare needs fulfillment system determines whether the question: (1) relates to prescription orders or payments, as in block 904, (2) relates to patient health topics, as in block 908, or (3) relates to insurance benefits, as in block 912. In some embodiments in which the question is received via a call center, the determination is made by providing relevant automated menu options to the patient and processing the patient's input. For example, in one embodiment, a patient is instructed to "select 1 for questions related to prescription orders or copayments, 2 for questions related to health and wellness, and 3 for questions related to your insurance benefits." Many other prompts and menu options may be used in other embodiments. In other embodiments, the determination may be made by an operator speaking to the patient. In still other embodiments, the patient submits the question via a web-based or application interface and is required to specify or select the topic to which the question pertains before submitting the question. In still other embodiments, the patient submits the question via the web-based or application interface and the system automatically parses the question to identify particular words it is programmed to associate with particular topics.

In FIG. 9, if it is determined that the patient's question relates to prescription orders or copayments, the patient or question is directed to the pharmacy that is filling the prescription, as in block 906. If the patient's question relates to health or wellness, the patient or question is directed to a professional services representative, as in block 910. Such representatives may be pharmacists, nurse practitioners, or other healthcare professional qualified to answer the patient's question. If the patient's question relates to insurance benefits, the healthcare needs fulfillment system directs the patient or question to the patient's prescription benefits manager, as in block 914. In some embodiments, if the patient's question does not relate to any of these topics, or if the patient fails to select one of the topics, the patient or question is directed to a patient services representative; in other embodiments, the patient is directed back to a main menu or interface (see block 916). At block 918, the healthcare needs fulfillment system determines whether the patient has one or more additional questions. If the patient has additional questions, the process of triaging and answering the question is repeated; if not, the patient is disconnected (see block 920) or returned to a homepage.

Figure 10:
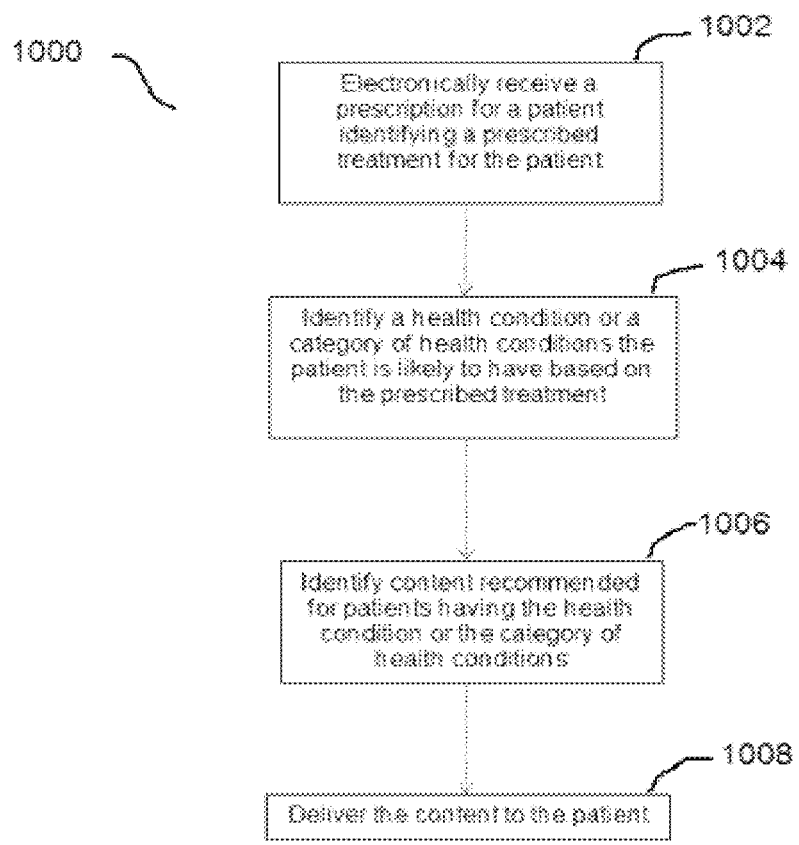
FIG. 10 is a flowchart illustrating an embodiment of a method for curating and delivering content to a patient, the method performed by a healthcare needs fulfillment system.

FIG. 10 provides a flowchart illustrating one embodiment of a method for curating and delivering content to a patient or other related patient or user, such as the patient's caregiver or physician. In various embodiments, the method is performed by a server programed to form a healthcare needs fulfillment system. The content of such embodiments is curated based on a patient's acquisition of a healthcare product or service, linking the acquisition event to a health condition. In various embodiments, the system then identifies and delivers to a patient or other user electronic health content relevant to a health state of the patient. The content may include, for example, articles and other written content and/or interactive web-based or mobile applications.

For example, as shown at block 1002 of FIG. 10, in some embodiments, a computer, such as a server managed by a plan manager, electronically receives a prescription identifying a prescribed treatment for a patient. The prescribed treatment may be any healthcare good or service. At block 1004, the computer identifies a health condition or a category of health conditions the patient is likely to have based on the prescribed treatment for the patient. For example, in some embodiments, the computer identifies the health condition or category of health conditions by searching a database to identify a product classification or service classification to which the prescribed treatment belongs. The classification may be from the National Drug Code Directory or other source, or the classifications may be proprietary and created in-house. The classifications may categorize each treatment according to the health condition or conditions it treats.

In some embodiments, as shown at block 1006, the computer also identifies content recommended for patients having the health condition or the category of health conditions. Content may be recommended, for example, if it has been identified as helpful for explaining a condition to a patient or helpful for encouraging disease management, health promotion, and/or treatment adherence. As one example, an application that stores blood sugar levels for users to review in an easy-to-use manner may be recommended to patients with diabetes. An application that provides a food log interface, calculates sodium content in food, and recommends low-sodium recipes may be recommended to patients with high blood pressure. Similarly, an application shown to have positive smoking cessation outcomes may be recommended to patients with high blood pressure who have indicated within their health profile that they are smokers. An application shown to encourage exercise may also be delivered to the patients with diabetes and/or high blood pressure. In some embodiments, a plan manager or outside vendor finds and recommends new applications and tags them as applicable to particular health conditions. In other embodiments, the computer identifies and classifies applications automatically by searching an application store for highly rated applications that have been tagged by the application's creator or the application store manager as applying to health and/or particular health conditions.

At block 1008, the computer delivers the content to the patient or a related user. The content may be delivered, for example, via email, text, push message or displayed within a web-based or mobile interface. In some embodiments, the content may be directly embedded within the delivery message. In other embodiments, a link, such as a hyperlink, is provided to connect the user to the content.

The healthcare needs fulfillment system of various embodiments described herein is intended to manage and coordinate the fulfillment of healthcare needs for thousands or even millions of patients. The system is configured to facilitate communications between hundreds, thousands, or millions of patients, pharmacies, providers, and physicians at any given time.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more example embodiments, the functions described may be implemented in hardware, software, or firmware executed on a processor, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes both the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the claims that follow rather than by the foregoing description. All variations coming within the meaning and range of equivalency of the claims are embraced within their scope.

What is claimed is:

1. A system for a prescription benefit manager configured to route and receive electronics prescription information across multiple platforms, the system comprising:

a network interface communicatively coupled to a computer network, the network interface including a receiver and a transmitter, the receiver configured to demodulate data received from the computer network including a plurality of prescriptions for a patient from at least one mobile user device, and the transmitter configured to transmit the plurality of prescriptions to a set of certified suppliers for fulfillment, wherein at least two of the set of certified suppliers are communicatively coupled to the network interface and are each selected to fill one or more of the plurality of prescriptions; and at least one processor communicatively coupled to the network interface, the at least one processor configured for:
  receiving, via the network interface, the plurality of prescriptions for the patient from the at least one mobile user device, the plurality of prescriptions identifying the patient and a prescribed treatment;
  applying, based on the plurality of prescriptions, a supplier selection criteria to select at least a first supplier and a second supplier from the set of certified suppliers, the first supplier being selected to fill a first prescription according to provisions of a prescription plan associated with the patient, and the second supplier being selected to fill a second prescription according to the provisions of the prescription plan associated with the patient, the first supplier being associated with a first system that does not share information with a second system of the second supplier;
  transmitting, via the network interface, the first prescription to the first supplier, and the second prescription to the second supplier for fulfillment;
  receiving, via the network interface, status updates from the first system of the first supplier and the second system of the second supplier, wherein the status updates include at least one of prescription receipt confirmation, fulfillment confirmation, and shipment confirmation from each of the first supplier and the second supplier; and
  transmitting, via the network interface, a single generated graphical mobile application interface having a format through which the status updates from the first system of the first supplier and the second system of the second supplier are together viewable simultaneously by the patient at the mobile user device, the status updates from the first system of the first supplier and the second system of the second supplier being viewable from a single page at the single generated graphical mobile application interface, the single generated graphical mobile application interface configured to display the status updates prior to a selection to interact, via a portal having a mobile application dashboard, with content related to the status updates from at least one of the first system of the first supplier or the second system of the second supplier, the status updates being selectable and accessible on the single page to interact, via the portal having the mobile application dashboard, with the content stored at least one of the first system of the first supplier or the second system of the second supplier, the portal having the mobile application dashboard configured to facilitate access between the mobile user device and at least one of the first system of the first supplier or the second system of the second supplier.

2. The system of claim 1, wherein the first supplier and the second supplier are selected to fulfill the plurality of prescriptions for the patient in a most effective manner with respect to at least one of costs, quality, and fulfillment speed as covered by the prescription plan associated with the patient.

3. The system of claim 1, wherein the processor is further configured for:
  calculating a copayment price owed by the patient for each of the plurality of prescriptions;
  accessing, via the network interface, account information for a financial account of the patient from a database;
  deducting, via the network interface, the copayment price from the financial account; and
  transmitting, via the network interface, a payment to the first supplier and the second supplier.

4. The system of claim 1, wherein the processor is further configured for:
  identifying the patient from each of the plurality of prescriptions;
  searching, via the network interface, a first database to identify the prescription plan to which the patient belongs; and
  searching, via the network interface, a second database to identify the supplier selection criteria associated with the prescription plan,
  wherein selecting the supplier selection criteria to apply to the plurality of prescriptions includes selecting the identified supplier selection criteria associated with the prescription plan.

5. The system of claim 1, wherein applying the supplier selection criteria comprises evaluating the set of certified suppliers and selecting the first supplier and the second supplier based on total price of adjudication.

6. The system of claim 1, wherein applying the supplier selection criteria comprises evaluating the set of certified suppliers and selecting the first supplier and the second supplier based on a combination of total price of adjudication, performance rating, and ancillary service offerings.

7. The system of claim 1, wherein the set of certified suppliers include suppliers that meet a minimum level of service requirements and have integrated into a healthcare needs fulfillment system.

8. The system of claim 1, wherein the first supplier and the second supplier may be selected from pharmacy, a provider of vitamins and nutritional supplements, a provider of durable medical equipment, or a provider of disposable medical supplies.

9. A non-transitory machine-readable medium storing instructions that, when executed by at least one processor, cause the at least one processor to perform operations comprising:
  receiving, via a network interface communicatively coupled to a computer network, a plurality of prescriptions for a patient from at least one mobile user device, the plurality of prescriptions identifying the patient and a prescribed treatment, the network interface including a receiver and a transmitter, the receiver configured to demodulate data received from the computer network including the plurality of prescriptions for the patient from the at least one mobile user device, and the transmitter configured to transmit the plurality of prescriptions to a set of certified suppliers for fulfillment, wherein at least two of the set of certified suppliers are communicatively coupled to the network interface and are each selected to fill one or more of the plurality of prescriptions;
  applying, based on the plurality of prescriptions, a supplier selection criteria to select at least a first supplier and a second supplier from the set of certified suppliers, the first supplier being selected to fill a first prescription according to provisions of a prescription plan associated with the patient, and the second supplier being selected to fill a second prescription according to the provisions of the prescription plan associated with the patient, the first supplier being associated with a first system that does not share information with a second system of the second supplier;

transmitting, via the network interface, the first prescription to the first supplier, and the second prescription to the second supplier for fulfillment;

receiving, via the network interface, status updates from the first system of the first supplier and the second system of the second supplier, wherein the status updates include at least one of prescription receipt confirmation, fulfillment confirmation, and shipment confirmation from each of the first supplier and the second supplier; and transmitting, via the network interface, a single generated graphical mobile application interface having a format through which the status updates from the first system of the first supplier and the second system of the second supplier are together viewable simultaneously by the patient at the mobile user device, the status updates from the first system of the first supplier and the second system of the second supplier being viewable from a single page at the single generated graphical mobile application interface, the single generated graphical mobile application interface configured to display the status updates prior to a selection to interact, via a portal having a mobile application dashboard, with content related to the status updates from at least one of the first system of the first supplier or the second system of the second supplier, the status updates being selectable and accessible on the single page to interact, via the portal having the mobile application dashboard, with the content stored at least one of the first system of the first supplier or the second system of the second supplier, , the portal having the mobile application dashboard configured to facilitate access between the mobile user device and at least one of the first system of the first supplier or the second system of the second supplier.

10. The non-transitory machine-readable medium storing instructions of claim 9, wherein the first supplier and the second supplier are selected to fulfill the plurality of prescriptions for the patient in a most effective manner with respect to at least one of costs, quality, and fulfillment speed as covered by the prescription plan associated with the patient.

11. The non-transitory machine-readable medium storing instructions of claim 9, wherein the operations further comprise:
calculating a copayment price owed by the patient for each of the plurality of prescriptions;
accessing, via the network interface, account information for a financial account of the patient from a database; and
deducting, via the network interface, the copayment price from the financial account; and
transmitting, via the network interface, a payment to the first supplier and the second supplier.

12. The non-transitory machine-readable medium storing instructions of claim 9, wherein the operations further comprise:
identifying the patient from each of the plurality of prescriptions;
searching, via the network interface, a first database to identify the prescription plan to which the patient belongs; and
searching, via the network interface, a second database to identify the supplier selection criteria associated with the prescription plan,
wherein selecting the supplier selection criteria to apply to the plurality of prescriptions includes selecting the supplier selection criteria associated with the prescription plan.

13. The non-transitory machine-readable medium storing instructions of claim 9, wherein applying the supplier selection criteria comprises evaluating the set of certified suppliers and selecting the first supplier and the second supplier based on a combination of total price of adjudication, performance rating, and ancillary service offerings.

14. The non-transitory machine-readable medium storing instructions of claim 9, wherein the set of certified suppliers include suppliers that meet a minimum level of service requirements and have integrated into a healthcare needs fulfillment system.

15. A computer-implemented method comprising:
receiving, using at least one processor and via a network interface communicatively coupled to a computer network, a plurality of prescriptions for a patient from at least one mobile user device, the plurality of prescriptions identifying the patient and a prescribed treatment, the network interface including a receiver and a transmitter, the receiver configured to demodulate data received from the computer network including the plurality of prescriptions for the patient from the at least one mobile user device, and the transmitter configured to transmit the plurality of prescriptions to a set of certified suppliers for fulfillment, wherein at least two of the set of certified suppliers are communicatively coupled to the network interface and are each selected to fill one or more of the plurality of prescriptions;

applying, using the at least one processor and based on the plurality of prescriptions, a supplier selection criteria to select at least a first supplier and a second supplier from the set of certified suppliers, the first supplier being selected to fill a first prescription according to provisions of a prescription plan associated with the patient, and the second supplier being selected to fill a second prescription according to the provisions of the prescription plan associated with the patient, the first supplier being associated with a first system that does not share information with a second system of the second supplier;

transmitting, using the at least one processor and via the network interface, the first prescription to the first supplier, and the second prescription to the second supplier for fulfillment;

receiving, using the at least one processor and via the network interface, status updates from the first system of the first supplier and the second system of the second supplier, wherein the status updates include at least one of prescription receipt confirmation, fulfillment confirmation, and shipment confirmation from each of the first supplier and the second supplier; and transmitting, using the at least one processor and via the network interface, a single generated graphical mobile application interface having a format through which the status updates from the first system of the first supplier and the second system of the second supplier are together viewable simultaneously by the patient at the mobile user device, the status updates from the first system of the first supplier and the second system of the second supplier being viewable from a single page at the single generated graphical mobile application interface, the single generated graphical mobile application interface configured to display the status updates prior to a selection to interact, via a portal having a mobile application dashboard, with content related to the status updates from at least one of the first system of the first supplier or the second system of the second supplier, the status updates being selectable and accessible on the single page to interact, via the portal having the mobile application dashboard, with the content stored at least one of the first system of the first supplier or the second system of the second supplier, the portal having the mobile application dashboard configured to facilitate access between the mobile user device and at least one of the first system of the first supplier or the second system of the second supplier.

16. The computer-implemented method of claim 15, wherein the first supplier and the second supplier are selected to fulfill the plurality of prescriptions for the patient in a most effective manner with respect to at least one of costs, quality, and fulfillment speed as covered by the prescription plan associated with the patient.

17. The computer-implemented method of claim 15, further comprising:
- calculating, using the at least one processor, a copayment price owed by the patient for each of the plurality of prescriptions;
- accessing, using the at least one processor and via the network interface, account information for a financial account of the patient from a database;
- deducting, using the at least one processor and via the network interface, the copayment price from the financial account; and
- transmitting, using the at least one processor and via the network interface, a payment to the first supplier and the second supplier.

18. The computer-implemented method of claim 15, further comprising:
- identifying, using the at least one processor, the patient from each of the plurality of prescriptions;
- searching, using the at least one processor and via the network interface, a first database to identify the prescription plan to which the patient belongs; and
- searching, using the at least one processor and via the network interface, a second database to identify the supplier selection criteria associated with the prescription plan,
- wherein selecting the supplier selection criteria to apply to the plurality of prescriptions includes selecting the selection criteria associated with the prescription plan.

19. The computer-implemented method of claim 15, wherein applying the supplier selection criteria comprises evaluating the set of certified suppliers and selecting the first supplier and the second supplier based on total price of adjudication.

20. The computer-implemented method of claim 15, wherein applying the supplier selection criteria comprises evaluating the set of certified suppliers and selecting the first supplier and the second supplier based on a combination of total price of adjudication, performance rating, and ancillary service offerings.

* * * * *